US010688221B2

(12) United States Patent
Mazza et al.

(10) Patent No.: US 10,688,221 B2
(45) Date of Patent: Jun. 23, 2020

(54) HUMAN LIVER SCAFFOLDS

(71) Applicant: UCL BUSINESS PLC, London, Greater London (GB)

(72) Inventors: Giuseppe Mazza, London (GB); Massimo Malago, London (GB); Paolo de Coppi, London (GB); Massimo Pinzani, London (GB)

(73) Assignee: UCL BUSINESS PLC, London, Greater (GB)

( * ) Notice: Subject to any disclaimer, the term of this patent is extended or adjusted under 35 U.S.C. 154(b) by 307 days.

(21) Appl. No.: 15/316,064

(22) PCT Filed: Jun. 2, 2015

(86) PCT No.: PCT/GB2015/051600
§ 371 (c)(1),
(2) Date: Dec. 2, 2016

(87) PCT Pub. No.: WO2015/185912
PCT Pub. Date: Dec. 10, 2015

(65) Prior Publication Data
US 2017/0112967 A1 Apr. 27, 2017

(30) Foreign Application Priority Data
Jun. 3, 2014 (GB) .................................... 1409858

(51) Int. Cl.
*A61L 27/38* (2006.01)
*A61M 1/16* (2006.01)
*A61L 27/36* (2006.01)
*G01N 33/50* (2006.01)
*G01N 33/68* (2006.01)

(52) U.S. Cl.
CPC ....... *A61L 27/3804* (2013.01); *A61L 27/3604* (2013.01); *A61L 27/3633* (2013.01); *A61L 27/3687* (2013.01); *A61L 27/3691* (2013.01); *A61L 27/3834* (2013.01); *A61M 1/16* (2013.01); *G01N 33/5044* (2013.01); *G01N 33/6893* (2013.01); *A61L 2430/28* (2013.01); *A61L 2430/40* (2013.01); *G01N 2800/085* (2013.01)

(58) Field of Classification Search
CPC ............. A61L 27/3604; A61L 27/3687; A61L 27/3691; A61L 27/3804; A61L 27/3834; A61L 2430/28; A61L 2430/40; A61L 27/3633; G01N 33/6893; G01N 33/5044; G01N 2800/085; A61M 1/16
See application file for complete search history.

(56) References Cited

U.S. PATENT DOCUMENTS

2005/0013870 A1  1/2005 Freyman et al.
2012/0064537 A1* 3/2012 Ross ........................... 435/6.13

OTHER PUBLICATIONS

Nari G.A. et al., "Preparation of a three-dimensional extracellular matrix by decellularization of rabbit livers", REV. ESP. ENFERM. DIG., 2013, vol. 105, No. 3, pp. 138-143. (Year: 2013).*
Wang et al., "Decellularized liver scaffolds effectively support the proliferation and differentiation of mouse fetal hepatic progenitors", J Biomed Mater Res., Apr. 1, 2014, pp. 1017-1025, vol. 102, No. 4, 1, John Wiley & Sons, Inc., Hoboken, NJ.
Faulk et al., "Decellularization and Cell Seeding of Whole Liver Biologic Scaffolds Composed of Extracellular Matrix", Journal of Clinical and Experimental Hepatology, Mar. 28, 2014, pp. 69-80, vol. 5, No. 1, Elsevier Inc., Amsterdam, Netherlands.
Guyette et al., "Perfusion decellularization of whole organs", Nature Protocols, May 29, 2014, pp. 1451-1468, vol. 9, No. 6, Nature Publishing Group, London, United Kingdom.
Crapo et al., "An overview of tissue and whole organ decellularization processes", Biomaterials, Jan. 19, 2011, pp. 3233-3243, vol. 32, No. 12,Elsevier Inc., Amsterdam, Netherlands.
Yagi et al., "Embryonic and Induced Pluripotent Stem Cells as a Model for Liver Disease", Crit Rev Biomed Eng., Jan. 1, 2009, pp. 377-398, vol. 37, No. 4-5, Begell House Publishers, Danbury, CT.
Uygun et al., "Organ reengineering through development of a transplantable recellularized liver graft using decellularized liver matrix", Nature Medicine, Jul. 1, 2010, pp. 814-820, vol. 16 No. 7, Nature Publishing Group, London, United Kingdom.
Mazza et al., "Decellularized Human Liver as a Natual 3D Scaffold for Organ Engineering and 3D-Disease Modeling", Hepatology, Nov. 7, 2014, p. 243A, vol. 60 No. 4 Suppl., John Wiley & Sons, Inc., Hoboken, NJ.
He et al., "Comparison of Methods for Whole-Organ Decellularization in Tissue Engineering of Bioartificial Organs", Tissue Engineering Part B: Reviews, Dec. 14, 2012, pp. 194-208, vol. 19, No. 3, Mary Ann Liebert, Inc, New Rochelle, NY.
Soto-Gutierrez et al., "A Whole-Organ Regenerative Medicine Approach for Liver Replacement", Tissue Engineering Part C: Methods, Apr. 19, 2011, pp. 677-686, vol. 17, No. 6, Mary Ann Liebert, Inc, New Rochelle, NY.

* cited by examiner

*Primary Examiner* — Satyendra K Singh
(74) *Attorney, Agent, or Firm* — Pamela J. Sherwood; Bozicevic, Field & Francis LLP

(57) ABSTRACT

This invention relates to methods for decellularising human liver tissue to produce human hepatic extracellular matrix (ECM) scaffolds, for example for use in therapy or disease modelling. The methods involve mechanically damaging cells in the tissue, for example by freeze thaw, and then subjecting the liver tissue to multiple cycles of osmotic stress, detergent treatment and protease and/or DNAase treatment to produce a decellularised human ECM scaffold.

12 Claims, 17 Drawing Sheets
(17 of 17 Drawing Sheet(s) Filed in Color)

A

B

HUMAN LIVER SCAFFOLDS

CROSS REFERENCE

This application claims the benefit of PCT Application No. PCT/GB2015/051600, filed Jun. 2, 2015, which claims benefit of G.B. Application No. 1409858.6, filed Jun. 3, 2014, which applications are incorporated herein by reference in their entirety.

This invention relates to the production of human hepatic extracellular matrix (ECM) scaffolds, for example for use in therapy, drug screening, biomarker identification or disease modelling Tissue engineering is an emerging field that is aimed at improving the quality of life for millions of people worldwide by restoring organ function. Tissue engineering combines cells and scaffolds for the development of 3D-structure in order to regenerate organs and to recapitulate disease in vitro. In addition to the restoration of organ function, tissue engineering can provide important biomedical applications including platforms for in vitro testing of therapeutic drugs and biological agents, for testing drug toxicity, for the evaluation of new devices and interventional techniques, and for the discovery of new biomarkers.

The human liver is a single organ that is divided in functional subunits, called segments (8 segments with individual portal and arterial supply, hepatic venous and biliary drainage) and sectors (more segments sharing vascular and biliary pedicles). These anatomical features allow the human liver to be partitioned in several functional sub-units that can be utilized in the practice of liver resection and segmental liver transplantation. The human liver is classically perfused with blood in anterograde fashion from the portal vein and hepatic arterial systems; the blood is drained by the hepatic venous system, the bile excreted by the liver by the biliary system.

The liver has a wide range of functions, including detoxification, protein synthesis, production of biochemicals necessary for digestion and a key role in carbohydrate and lipid metabolism. The liver is necessary for survival; there is currently no way to compensate for the absence of liver function in the long term. This unique function is orchestrated by parenchymal and non-parenchymal cells strictly organized in a network of extracellular matrix (ECM)-proteins which constitute a 3D scaffold.

Liver disease due to viral infection, alcohol and other conditions is increasing and currently causes 10,000 deaths each year in the UK and 32,000 deaths in the US. Liver transplantation is the only effective treatment for advanced acute or chronic liver disease and is associated with excellent long term survival and quality of life. However availability is limited and demand is increasing. Waiting times are increasing with 15% to 25% of people suitable for liver transplantation dying or becoming too unwell while on the waiting list. Developing an artificial liver will reduce the deaths due to liver disease and will provide a solution for patients in whom organ transplant is not currently available.

In addition, all of the models used to investigate hepatic fibrosis (HF) and the development of hepatocellular carcinoma (HCC) have inherent problems. Thus, studies in 2D monolayer single cell cultures or co-cultures have formed the backbone of most in vitro studies, but are largely remote from real-life. Further, most animal models, although sharing many characteristics with human disease do not share the same mode of gene expression as humans and their validity as an in vivo model is limited. Thus, there is an unmet need to develop models which reproduce the complexity of human disease.

In recent years, the possibility of obtaining suitable scaffolds to be used for repopulation with human cells has been evaluated using the livers of large animals, such as pigs and sheep. However, besides inherent differences in the metabolic capabilities of the liver, the extracellular ECM scaffold has distinct macroscopic and microscopic features in different species. In particular, the segmentation and lobulation of the human liver is not as evident as in other species. In addition, the microscopic lobular anatomy and structure of the human liver is unique and different from other mammals, such as pig, since the fibrotic boundaries between liver lobules are not present in humans (and the human lobular architecture is without formal structural boundaries). The presence of fibrotic boundaries typical of pig livers represents a major problem for the use of scaffolds obtained from pig liver in transplantation in humans, following repopulation with human cells. Indeed the different architecture in pigs could lead to portal hypertension, since the bridging predisposes to flow barriers in the normal human liver.

The in vitro development of 3D human liver tissue which recapitulates the composition and organization of the 3D human ECM proteins is one of the main challenges in the tissue engineering field. A promising approach involves the establishment of biological scaffolds by a process of tissue decellularisation. However, previous reports from other authors have failed to obtain 3D human liver scaffold due to intrinsic difference in macro and micro structure, peculiar to humans and distinctively different than in other mammals. Whilst the decellularisation of mouse, rat, ferret, sheep and pig livers has been reported, there are no publications describing the successful generation human liver biological scaffold.

The present inventors have recognised that regimes comprising one or more cycles of treatment with sets of different cell damaging agents may be used to decellularise human liver tissue without damaging the extracellular matrix. This may be useful in the reproducible production of acellular scaffolds that maintain the architecture and morphology of the extracellular matrix of the human liver.

An aspect of the invention provides a method of producing a human liver scaffold comprising
 (i) providing human liver tissue,
 (ii) mechanically damaging the cells in the tissue,
 (iii) subjecting the cells in the tissue to osmotic stress,
 (iv) optionally exposing the tissue to a protease and/or DNAase, and
 (v) exposing the tissue to a detergent, and
 (vi) repeating each of step (iii), step (iv) and step (v), and optionally step (ii), one or more times,
 thereby producing a human liver scaffold.

In some embodiments, the method may comprise step (iv). In other embodiment, step (iv) may be omitted (i.e. the method does not include step (iv)).

A human liver scaffold produced by the claimed methods consists of acellular human liver extracellular matrix (ECM) (i.e. the scaffold is decellularised) and retains the three dimensional architecture and bioactivity of the ECM of the source liver tissue.

After the cells are mechanically damaged, the liver tissue is exposed to the different decellularisation reagents (i.e. osmotic stress reagents, protease/DNAase and detergents) sequentially. Steps (iii), (iv) and (v), and optionally step (ii), may be performed one or more times in any order to decellularise the scaffold. In some embodiments, the liver tissue may be exposed to multiple cycles comprising any one, two or all three of steps (iii), (iv) and (v), and optionally step (ii), in any order.

In some embodiments, step (ii) may be repeated one or more times. For example, the liver tissue may be exposed to multiple cycles comprising step (ii). This may for example be useful when non-freeze thaw techniques, such as ultrasound, are used to mechanically damage the cells.

Preferably, the liver tissue is subjected to flow shear stress during steps (iii) to (vi). This facilitates the penetration of decellularisation reagents within the tissue e.g. into the hepatic sinusoid and detaches cells and cell debris from the extracellular matrix (ECM).

Any convenient technique may be used to generate flow shear stress in the liver tissue, including perfusion, agitation or negative pressure. Preferably, flow shear stress is generated in the human liver tissue by perfusion or agitation.

The choice of technique for generating flow shear stress may depend on the liver tissue or the application. For example, whole livers, single lobe-sectors, segments or other hepatic structural units may be perfused with decellularisation reagents to generate flow shear stress. Small liver samples, such as liver tissue cubes (LTCs), may be immersed in the decellularisation reagents and agitated to generate flow shear stress.

Human liver tissue for decellularisation as described herein may be obtained from human livers that are unsuitable for clinical use in transplantation. Suitable livers may be obtained in accordance with relevant national laws and ethical guidelines.

In some embodiments, the liver tissue may be normal tissue which does not display pathology associated with damage or disease.

In other embodiments, the liver tissue may be pathological tissue which displays pathology associated with damage or disease. For example, liver tissue may be fatty, fibrotic, inflamed or display one or more other features associated with disease or damage. In some embodiments, pathological liver tissue may display pathology associated with acute or chronic liver disease, including viral infections, such as hepatitis A, B, C, D or E, alcohol or toxin damage, hepatic fibrosis (HF), non-alcoholic fatty liver disease (NAFLD), primary sclerosing colangitis (PSC), primary biliary cirrhosis (PBC), alcoholic liver disease, ischaemic hepatitis, giant cell hepatitis, and liver cancers, such as hepatocellular carcinoma (HCC). Alternatively, pathological liver tissue may display pathology associated with other diseases that affect the liver, such as amyloidosis.

Liver scaffolds produced from pathological liver tissue may have a different structure and composition from scaffolds produced from healthy liver tissue. For example, the morphology of the pathological scaffold or the amounts or relative amounts of ECM components, such as collagen, tenascin and laminin may be altered in scaffolds from pathological liver tissue compared to healthy liver tissue. This may be useful in obtaining specific disease-modified liver scaffolds for disease modelling.

Pathological liver tissue may be obtained from an individual with a liver disease or a disease that affects the liver (e.g. a disease characterised by liver damage or altered liver function).

Methods of obtaining and storing liver tissue for decellularisation as described herein are well-known in the art. For example, the liver may be heparinized to prevent coagulation and/or perfused with a cryoprotectant agent to reduce or prevent tissue disruption after thawing.

Human liver tissue suitable for decellularisation as described herein may include whole livers or parts of a liver, including hepatic functional units, such as lobe-sectors, segments or sub-segments, or small samples or sections of a liver.

A part of a liver may comprise one or more hepatic functional units, such as lobe-sectors, segments or sub-segments. Suitable functional units may be vascularised and/or comprise a vasculo-biliary pedicle. For example, the liver tissue may comprise sub-segments of S8 of the human liver, one or more of segments S1 to S8 of the human liver or a multi-segment portion, such as left lateral (S2+S3±S1), left liver (S2+S3+S4+S1), the right liver (S5+S6+S7+S8), right lateral liver (S6+S7), right extended liver (S4+S5+S6+S7+S8+S1). In some preferred embodiments, the liver tissue may be the left lateral (S2+S3±S1) or left liver (S2+S3+S4+S1) part of a human liver.

The amount and mass of the liver tissue that is decellularised as described herein may depend on the intended use of the scaffold. For example, the mass of the liver tissue that is decellularised for use in an implant may depend on the body mass of the individual and the amount of functional liver tissue in the individual.

In other embodiments, the part may be a small non-vascularized liver section or wedge of 0.2-2 cm in width, length and/or diameter, preferably 0.2-1.25 cm, more preferably 0.2-1.0 cm (e.g. a section with a volume of 0.008 $cm^3$ to 2 $cm^3$, more preferably 0.008 $cm^3$ to 1 $cm^3$, for example about 0.125 $cm^3$). Preferably, the section is of a suitable size for manipulation in standard laboratory vessels, such as multi-well plates, and may be for example approximately cubic with sides of about 0.5 cm.

Small non-vascularized liver sections or wedges may be useful in reproducing the complexity of 3D human microenvironment in small scale for liver disease modelling, drug screening, biomarker identification and validation and the development of disease diagnostics. Suitable sections may be obtained using a tissue dicer, punch biopsy, needle biopsy or by simple scalpel cleavage of sections, such as cubes, of parenchyma.

Multiple liver parts for decellularisation as described herein may be obtained from one liver, thus one donor human liver may be used for more than one patient or may be used for both clinical and disease modelling applications.

A method may comprise providing a discarded whole human liver or a part thereof. The whole human liver may be divided into one or more parts before decellularisation as described herein.

In some embodiments, the human liver tissue may be treated with cryoprotectants before step (i). For example, the tissue may be treated with intracellular and/or extracellular cryoprotectants before being freezing. Suitable cryoprotectants include DMSO, ethylene glycol, propylene glycol, glycerol, 2-methyl-2,4, pentanediol (MPD), and sucrose.

In the first decellularisation step, the cells in the human liver tissue are subjected to mechanical damage to facilitate their destruction and removal. The cells may be mechanically damaged by any suitable technique that damages the cells of the liver tissue without affecting the extracellular matrix, including freeze/thaw, sonication, or high intensity focussed ultrasound (HIFU).

In some embodiments, mechanical damaging techniques may not be repeated after the initial treatment. For example, such as freeze/thaw treatment after exposure to other decellularisation reagents may lead to ECM damage.

In other embodiments, the cells in the liver tissue may be subjected to mechanical damaging one or more times after the initial treatment (e.g. in step (vi) above). For example, the tissue may be subjected to HIFU or sonication one or more times.

Preferably, the cells are mechanically damaged by subjecting the human liver tissue to one or more freeze/thaw cycles. For example, the tissue may be frozen at −20° C. or less, preferably −50° C. or less, −60° C. or less, −70° C. or less, and then thawed one or more times. Frozen tissue may be conveniently thawed at 4° C. to 37° C. In some preferred embodiments, the tissue may be thawed at about 4° C. to minimise temperature gradients within the tissue that may damage the ECM. For example, the tissue may be frozen at about −80° C. for 24 hours or more and then thawed at about 4° C.

Human liver tissue that is subjected to freeze/thaw is preferably dry to prevent ECM damage. In some embodiments, human liver tissue may be dried before the freeze/thaw step, for example by 5 to 30 mins exposure at room temperature.

The liver tissue may be subjected to freeze/thaw in an isotonic buffer, such as saline, such as 0.90% (w/v) NaCl, or PBS.

Following mechanical damage, the human liver tissue is decellularised by a series of sequential exposures to osmotic reagents, enzyme(s) and detergents (i.e. decellularisation reagents). These sequential exposures to different decellularisation reagents detach cells and cell debris from the extracellular matrix (ECM) and remove them from the liver tissue.

Osmotic stress causes lysis of the cells in the liver tissue and amplifies the effects of the mechanical damage. Osmotic stress may be induced by exposing the tissue to one or more osmotic reagents which have a different osmotic pressure to the cells in the tissue (i.e. a non-isotonic reagent). The tissue may be exposed to one or more hypotonic reagents which have a lower osmotic pressure than the cells and subject the cells to a hypotonic environment and/or one or more hypertonic reagents which have a higher osmotic pressure than cells and subjects the cells to a hypertonic environment. Hypotonic reagents may be preferred in some embodiments.

Hypertonic reagents may be useful, for example, in dissociating DNA from proteins. Suitable hypertonic reagents are well known in the art and include saline (e.g. >0.9% (w/v) NaCl, for example 3% to 7% (w/v) NaCl), which may optionally be buffered for example with phosphate, borate or tris, and polyethylene glycol solutions.

Hypotonic reagents may be useful for example in inducing cell lysis through simple osmotic effects with minimal changes in the molecules and architecture of the ECM. Suitable hypotonic reagents are well known in the art and include water, deionised water and saline of <0.9% (w/v) NaCl.

In some embodiments, enzymes are used to disrupt cellular and sub-cellular structures in the liver tissue and break cell linkages with the ECM. For example, proteins in the tissue may be degraded with a protease. Suitable proteases are well-known in the art and include trypsin. The liver tissue may be exposed to 0.0025-0.25% (w/v) trypsin, for example 0.025% trypsin. In some embodiments, the liver tissue may be exposed to a protease in solution with a chelating agent, such as EDTA, which chelates divalent metallic ions, such as $Ca^{2+}$, and disrupts cell adhesion to the ECM.

In the series of exposures to decellularisation reagents, the liver tissue may be exposed to a protease before exposure to a detergent. This allows cells or cellular material that is detached from the ECM by the protease to be washed out of the tissue by the detergent.

In other embodiments, liver tissue may be decellularised without the use of a protease.

In some embodiments, genomic structures and deoxyribonucleic acid in the tissue may be degraded with a deoxyribonuclease (DNAase).

Suitable DNAses are well known in the art and include DNAseI. The liver tissue may be exposed to 1000-10000 KU DNAse 1, for example about 2000 KU DNAse 1. Deoxyribonuclease treatment may be particularly useful in methods which employ a gentle detergent, such as sodium deoxycholate. In some embodiments, the DNAse may be in a salt balanced solution, for example 1M NaCl. In other embodiments, liver tissue may be decellularised without the use of a deoxyribonuclease.

In some embodiments, liver tissue may be decellularised without the use of a deoxyribonuclease or a protease.

Detergents solubilise lipids and fats in the tissue and facilitate the removal of cellular debris from the ECM.

Detergents may include anionic detergents, such as sodium dodecyl phosphate (SDS), sodium deoxycholate (SdC), and Triton™ X-200. For example, the liver tissue may be exposed to 0.01 to 5% SDS, for example 0.01-1% SDS; 0.01 to 5% sodium deoxycholate (SdC), for example about 4% sodium deoxycholate; and/or 0.01 to 5% Triton™ X-200, for example 3% Triton™ X-200.

Detergents may include non-ionic detergents, such as polyethylene glycol and Triton™ X100, e.g. polyethylene glycol p-(1, 1, 3, 3-tetramethylbutyl)-phenyl ether. For example, the liver tissue may be exposed to 0.01 to 5% Triton™ X-100, or 1 to 3% Triton™ X-100, for example 3% Triton™ X-100.

Detergents may include zwitterionic detergents, such as CHAPS (3-[(3-Cholamidopropyl)dimethylammonio]-1-propanesulfonate), sulfobetaine-10 (3-(Decyldimethylammonio)propanesulfonate), sulfobetaine-16 (n-Hexadecyl-N,N-dimethyl-3-ammonio-1-propanesulfonate), and Tri(n-butyl)phosphate. For example, the liver tissue may be exposed to 0.01 to 5% zwitterionic detergent, for example 0.01-1% zwitterionic detergent.

Numerous other suitable detergents are known in the art and available from commercial sources (e.g. Sigma Aldrich Co LLC, MO, USA).

In some preferred embodiments, the liver tissue may be exposed to a first detergent and a second detergent in separate steps. For example, a method may comprise (a) exposing the tissue to an anionic detergent, such as SDS and (b) exposing the tissue to a non-ionic detergent, such as Triton™ X-100.

In some embodiments, the concentration of the decellularisation reagent that is employed in each treatment step may be increased progressively to a maximum value. For example, the concentration of detergent that is employed may be increased progressively to a maximum value. The initial detergent concentration may be sufficiently low to avoid the formation of aggregates or clumps of cell material that occlude vessels in the liver tissue. After the initial detergent treatment, the concentration of the detergent is increased to effectively remove all the cellular material.

Step (iii) may therefore comprise exposing the liver tissue to the detergent at progressively increasing concentrations. Preferably, the highest concentration is employed when step (iii) is repeated. For example, the liver tissue may be exposed to 0.005%-0.02% SDS, for example about 0.01% SDS, followed by exposure to 0.05% SDS to 0.2% SDS, for example about 0.1% SDS, followed by exposure to 0.5% SDS to 2% SDS, for example about 1% SDS.

Subsequent detergent treatment steps (i.e. repetitions of step iii) may employ 0.5% SDS to 2% SDS, for example about 1% SDS.

In some preferred embodiments, the liver tissue may be exposed to the decellularisation reagents by perfusing the tissue with the reagents. Preferably, the liver tissue is perfused in a retrograde direction and not in an antegrade direction.

Suitable techniques for tissue perfusion in vitro are well-known in the art. For example, liver tissue may be prepared for perfusion by insertion of a cannula into a vessel, duct or cavity, for example the vena cava or the hepatic vein. The cannulated tissue may then be perfused with the decellularisation reagents via the cannulation.

In preferred embodiments, the rate of perfusion of the liver tissue with the decellularisation reagents is not constant. For example, the initial rate of perfusion of the tissue may be low (e.g. <0.99 ml/min/gram of tissue) to avoid architectural damage to the liver tissue. Over the course of the decellularisation, as steps (iii) to (v) are repeated, the liver tissue becomes less resistant to perfusion and the rate of perfusion is increased (e.g. >1 ml/min/gram of tissue). This increases the flow shear stress in the tissue.

Preferably, the perfusion rate is progressively increased to a maximum value (compensation phase) over two or more cycles of exposure to decellularisation reagents and then maintained at or near this maximum value (stabilization phase). In some embodiments, the tissue may be initially perfused with the decellularisation reagents at a flow rate of 0.1-1.99 ml/min/gram of tissue, for example 0.5 to 1.5 ml/min/gram, and progressively increased to 2-20 ml/min/gram of tissue, for example 2-8 ml/min/gram. In other embodiments, the tissue may be initially perfused with the decellularisation reagents at a flow rate of 0.01-0.99 ml/min/gram of tissue, for example, 0.5 to 1.5 ml/min/gram, and progressively increased, for over 5 to 10 days, preferably about 9 days, to 1-10 ml/min/gram of tissue, for example 2-8 ml/min/gram.

The liver tissue may be perfused with each decellularisation reagent for about 0.004 hours to about 5 hours per gram of solid tissue (for tissue samples >40 grams) or about 2 hours to about 12 hours per gram of solid tissue (for tissue samples <40 grams).

For example, decellularisation as described herein may take 1-60 days, for example 7-60 days, depending on the initial mass of the liver tissue.

The order in which the tissue is perfused with the different decellularisation reagents may vary, subject to the liver tissue being perfused with each reagent at least once, at least twice or at least three times over the course of the decellularisation.

The order of exposure to the different detergents is based on their different mechanism of actions. The mechanical damage (first step) promotes an intense cellular disruption. The exposure to hypotonic solutions (second step) amplifies the cell lysis, while washing out cellular materials. After that, the liver tissue is optionally exposed to proteolytic enzymes (third step) to remove cellular materials attached to the ECM. Lastly, the liver is exposed to the different detergents (fourth step) to effectively wash out cellular materials. The four steps can be repeated in function of the flow rate.

The mechanical damage of step (i) promotes intense cellular disruption within the human tissue. Typically, step (i) is performed once at the beginning of decellularisation, but in some embodiments, HIFU or sonication mediated mechanical damage may be induced more than once during the decellularisation. The cell lysis caused by the mechanical damage is amplified by osmotic stress in step (ii). Exposure to osmotic solutions also washes cellular debris out of the tissue. The liver tissue is then optionally exposed to DNase or preferably a proteolytic enzyme in step (iii) to remove cellular material that is attached to the ECM. Lastly, the liver is exposed to one or more detergents in step (iv) to wash cellular materials out of the tissue. Steps (iii) to (iv) can be repeated one or more times with increasing flow shear stress.

In some embodiments, a method may comprise repeating steps (iii) to (v) in the following sequence by perfusion through the liver tissue; (iii), (iv), (iii), (iv) (v), [(iii), (v)]$_n$, (iii), (iv), [(iii) (v)]$_n$, where n is 1 to 25. A suitable perfusion decellularisation regime is shown in Table 1. Optionally, step (ii) may also be repeated one or more times in the method.

Decellularisation reagents may be perfused through a whole liver or a functional unit thereof to generate an ECM scaffold that matches the source tissue size and structure. In some embodiments, this scaffold may be subsequently repopulated with cells in order to obtain functional hepatic tissue which may, for example, be suitable for direct transplantation into humans.

In some embodiments, the liver tissue may be pathological. Perfusion of pathological liver tissue with decellularisation reagents may be useful, for example, in the generation of an ECM scaffold that can be repopulated with cells for 3D disease modelling.

In other preferred embodiments, human liver tissue may be exposed to the decellularisation reagents by immersing the tissue in the reagents and subjecting it to agitation, for example on a rotary agitator.

Sections or samples of liver tissue may be agitated in decellularisation reagents in order to generate scaffolds that reproduce the complexity of 3D human microenvironment in small scale for liver disease modelling. The samples may be of normal or pathological liver tissue. Suitable samples may range from 0.2-2 cm or 0.2-1.0 cm in width/length or diameter. For example, the sample may be a section or cube of approximately 5 mm width, termed a "liver tissue cube" (LTC) herein.

Liver tissue samples for decellularisation through an agitation regime may be obtained using a tissue dicer, needle biopsy, punch biopsy or by simple scalpel cleavage of sections or cubes of human liver parenchyma, in accordance with standard techniques.

Agitation of liver tissue immersed in the decellularisation reagents may subject it to flow shear stress. Suitable agitation may include rotary shaking, for example in a rotary agitator or magnetic stirrer, at 100-1000 rpm, preferably about 900 rpm.

In some embodiments, the agitated tissue may be subjected to one or more cycles of;
  (a) exposing the tissue to an osmotic stress reagent, for example a hypotonic or hypertonic reagent,
  (b) exposing the tissue to a protease and/or DNAase, and
  (c) exposing the tissue to a detergent, wherein (a), (b) and (c) may occur in any order in each cycle.

For example, the tissue may be subjected to one or more cycles of;
  (a) exposing the tissue to a hypotonic reagent,
  (b) exposing the tissue to a detergent, and
  (c) exposing the tissue to a DNAase,
  For example, 1 to 25 cycles may be performed.

The tissue may be exposed to the hypotonic reagent, such as water, for 12 to 36 hours, preferably about 24 hours. The tissue may be exposed to the hypotonic reagent at 4° C.

The tissue may be exposed to the detergent, such as SdC, for example 4% SdC, for 4 to 12 hours, preferably about 6 hours. The tissue may be exposed to the detergent at ambient temperature.

The tissue may be exposed to the DNAse for about 3 hours. The tissue may be exposed to the DNAse at ambient temperature. For example, the tissue may be exposed to 2000 KU DNAse1 in 1M NaCl.

A method may further comprise exposing the tissue to a wash solution following exposure to any of the decellularisation reagents set out above. The tissue may be washed between one or more of the above steps and/or between cycles e.g. between steps (a) and (b), between steps (b) and (c) and/or after step (c) and before any cycle repetition. For example, the tissue may be washed with phosphate buffered saline (PBS) or PBS supplemented with an antibiotic-antimycotic agent for 5 to 30 mins at ambient temperature, preferably about 5 mins. Suitable antibiotic-antimycotic agents are well known in the art.

In other embodiments, the tissue may be subjected to one or more cycles of;
(a) exposing the tissue to a hypotonic reagent, such as water,
(b) exposing the tissue to a protease, such as trypsin, preferably in dH$_2$O (deionised water).
(c) exposing the tissue to an first detergent, for example an anionic detergent, such as SDS,
(d) exposing the tissue to a second detergent, for example an ionic detergent, such as Triton™ X-100.

The tissue may be exposed to the hypotonic reagent, such as water, for 15 to 30 mins at ambient temperature.

The tissue may be exposed to the protease, for example 0.025% trypsin in dH$_2$O (deionised water) or EDTA for 12 to 36 hours at ambient temperature.

The tissue may be exposed to the first detergent, for example 0.01-1% SDS for 12 to 96 hours at ambient temperature.

The tissue may be exposed to the second detergent, for example 0.01-3% Triton™ X100 for 12 to 72 hours at ambient temperature.

Between one or more of the above steps and/or between cycles, the tissue may be washed. The tissue may be washed between one or more of the above steps and/or between cycles e.g. between steps (a) and (b), between steps (b) and (c), between steps (c) and (d) and/or after step (d) and before any cycle repetition. For example, the tissue may be washed with phosphate buffered saline (PBS) or PBS supplemented with an antibiotic-antimycotic agent for 5 mins to 3 hours, for example 30 mins to 1 hour, at ambient temperature.

For example, a method may comprise subjecting the agitated tissue to one or more cycles of;
(a) exposing the tissue to deionised water,
(b) washing the tissue in PBS,
(c) exposing the tissue to SdC,
(d) washing the tissue in PBS
(e) exposing the tissue to DNAase, and
(f) washing the tissue in PBS.

Steps (a) to (f) may be repeated 4-8 times, preferably about 4 times.

Suitable agitation may be provided by an orbital shaker at 600-1200 rpm, for example, about 900 rpm; or a magnetic stirrer at 150-600 rpm, for example 300-400 rpm.

In some embodiments, the tissue may be exposed to water and dextrose solution alternatively for 4-12 hours, for example 8 hours, before step (a).

In other embodiments, a method described above may further comprise;
(f) exposing the tissue to a hypertonic agent, such as 9% saline.

The duration of each cycle of exposure to the decellularisation reagents may be 2-3 days. The total time to decellularise the scaffold using an agitation regime may be 2.5-25 days, for example about 8 days.

Following decellularisation, the scaffold may be sterilised, for example by exposure to a sterilising agent. Suitable sterilising agents include γ-irradiation, electrolysed water and chemical agents, such as paracetic acid. The scaffold may be exposed to 0.01% paracetic acid and 4% ethanol, for example for 30 mins to 2 hours.

The scaffold may be perfused with the sterilising agent or immersed in the sterilising agent and subjected to agitation, as described herein.

Following decellularisation and sterilisation, the liver scaffold may be tested, for example for the absence of cells and/or the presence of ECM components, such as collagen, laminin, elastin, proteoglycans, hyaluronic acid, fibronectin, growth factors and extracellular proteases.

Suitable techniques, including macroscopic visualisation, microscopy and immunohistochemical techniques, are well-known in the art.

Decellularised human liver scaffolds may lack detectable myofilaments, endothelial cells, smooth muscle cells, and cell debris and nuclei in histologic sections using standard histological staining procedures.

Decellularised human liver scaffolds produced as described herein preserve the 3D organ morphology and architecture and the ECM bioactivity of the source liver tissue.

In some embodiments, the architecture and morphology of a decellularised liver scaffold produced by the methods described above may be confirmed by electron microscopy.

Depending on the source tissue, the liver scaffold may comprise a normal ECM or may be a disease modified ECM. For example, the liver scaffold may comprise one or more structural alterations that are characteristic of a liver disease or pathology.

The human liver scaffolds allow effective attachment, migration, proliferation and three-dimensional organization of cells that are cultured in the scaffold. The decellularised human liver scaffold may also provide bioactive molecules and bioinductive properties, which maintain cell phenotype and functional properties, and encourage production of tissue specific matrix.

Following production of decellularised human liver scaffold as described herein, a method may comprise re-populating the scaffold with cells to produce artificial liver tissue.

Suitable cells include human primary and cell line liver cells (e.g. hepatic stellate cells, Kupffer cells, Liver Sinusoidal Cells), primary hepatocytes, endothelial cells, iPSCs or cells derived from patient-specific iPSCs, embryonic stem cells (hESCs), mesenchymal stem cells (hMSC), hepatocyte derived mesenchymal stem cells (HDMSC) fetal stem cells (e.g. amniotic fluid stem cells and fetal liver cells), cancer cells and endothelial progenitor cells (EPC).

In some embodiments, the decellularised human liver scaffold may be repopulated with autologous human cells obtained from a patient, for example to produce artificial liver tissue for implantation into the patient. In other embodiments, the decellularised human liver scaffold may be repopulated with allogeneic human cells i.e. cells derived from a different human individual, for example to produce artificial liver tissue for implantation into the patient. In some embodiments, the allogeneic human cells may be screened for immunocompatibility with the patient before implantation.

The decellularised scaffold may be repopulated by seeding the scaffold with cells into the scaffold and culturing under suitable conditions. For example, the cells may be directly injected in the parenchyma of the decellularised scaffold; perfused via the main vascular accesses; and/or dropped on the surface of the decellularised scaffold Other aspects of the invention provide the decellularisation of liver tissue from a non-human animal, such as a non-human primate, pig, sheep, horse or cow, using the methods described above mutatis mutandis, to produce a non-human liver scaffold. The non-human scaffold may be repopulation with human cells as described above to produce artificial liver tissue comprising human cells within a non-human ECM scaffold. This may be useful in the production of artificial liver tissue for implantation into patients.

In some embodiments, a decellularised human liver scaffold or artificial liver tissue produced as described herein, may be dissected to remove one or more liver tissue structures, such as ducts and vessels. Structures removed from a decellularised human liver scaffold may be optionally repopulated with cells as described above. Structures removed from the liver scaffold or tissue may be useful for transplantation, for example to treat disease as described below, or disease modelling.

Other aspects of the invention provide a human liver scaffold or artificial liver tissue produced by a method described above.

Human liver scaffolds produced as described herein are acellular and display the extracellular matrix pore structure and morphology of the source liver tissue. Human liver scaffolds produced from fatty source liver tissue display the increased lipid content characteristic of the source tissue. Human liver scaffolds produced from fibrotic source liver tissue display the increased ECM components characteristic of the source tissue.

The scaffold or tissue may be useful for disease modelling. Suitable scaffolds may be derived from normal liver tissue or pathological liver tissue, as described above.

A method of disease modelling may comprise;
   providing a human liver scaffold or artificial human liver tissue produced as described above
   determining the effect of a compound, drug, biological agent, device or therapeutic intervention on the scaffold or tissue or the cells therein.

Methods described herein may be useful in modelling liver diseases or diseases affecting the liver, such as liver fibrosis, liver cancer and metastases, liver drug toxicity, post-transplant immune responses, and autoimmune hepatitis.

Biological agents may include viruses, such as HBV and HCV.

Decellularised liver scaffolds may be useful for the diagnosis of liver disease. Suitable scaffolds may be derived from liver tissue from an individual suspected of having liver disease.

A method of diagnosing liver disease in a human individual may comprise;
   providing a sample of liver scaffold from the individual produced as described above
   determining the presence and amount of one or more liver scaffold proteins in the sample.

The presence and amount of liver scaffold proteins in the sample may be indicative of the presence of liver disease in the individual.

The scaffold or tissue may be useful in therapy, for example for the replacement or supplementation of liver tissue in an individual.

A method of treatment of a liver disease may comprise;
   implanting a human liver scaffold or artificial human liver tissue produced as described above into an individual in need thereof.

The implanted scaffold or tissue may replace or supplement the existing liver in the individual.

Another aspect of the invention provides a human liver scaffold or artificial human liver tissue produced as described above for use in the treatment of liver disease or dysfunction in an individual.

For example, a human liver scaffold or artificial human liver tissue may be implanted in an individual to regenerate a complete new liver or to improve the repair of a damaged liver, or may support the liver function of the individual from outside the body.

Other aspects of the invention provide the decellularisation of human pancreas tissue, using the methods described above mutatis mutandis, to produce a human pancreas scaffold. The human pancreatic scaffold may be repopulation with human cells as described above to produce artificial pancreatic tissue comprising human cells within a human ECM scaffold. This may be useful in the production of artificial pancreatic tissue for implantation into patients.

For example, another aspect of the invention provides a method of producing a human pancreas scaffold comprising
   (i) providing human pancreatic tissue,
   (ii) mechanically damaging the cells in the tissue,
   (iii) subjecting the cells in the tissue to osmotic stress,
   (iv) exposing the tissue to a protease and/or DNAase, and
   (v) exposing the tissue to a detergent, and
   (vi) repeating each of step (iii), step (iv) and step (v), and optionally step (ii), one or more times,
   thereby producing a human pancreas scaffold.

Human pancreas scaffolds may be produced in accordance with any of the methods described above for liver scaffolds, except that the terms "liver" and "hepatic" are replaced by "pancreas" and "pancreatic".

Decellularised human pancreas scaffold produced by a method described above may be repopulated with cells produce artificial pancreatic tissue.

Aspects of the invention provide decellularised human pancreas scaffold and artificial pancreatic tissue produced by the methods described herein.

Human pancreas scaffold and artificial pancreatic tissue may be used for disease modelling, diagnosis and methods of treatment as described above mutatis mutandis for liver scaffolds and tissue.

Another aspect of the invention provides a bioreactor comprising;
   a human liver scaffold produced as described above;
   an input conduit for the introduction of culture medium to the scaffold; and
   an output conduit for the exit of culture medium from the scaffold.

Preferably, the liver scaffold is seeded with human cells, for repopulation of the scaffold. This may be useful in the production of artificial liver tissue.

Suitable cells for seeding the scaffold are described above.

The bioreactor may further comprise a culture medium reservoir. The input conduit may be connectable or adapted for connection to the reservoir, such that the scaffold in the bioreactor is perfused with the culture medium from the reservoir, so as to allow recellularisation of the scaffold by the cells seeded into the scaffold.

The bioreactor may further comprise a tissue chamber for accommodating the liver scaffold.

The scaffold may be contained in a suitable culture medium in the bioreactor.

The liver scaffold in the tissue chamber and the culture medium in the reservoir may be maintained at 37° C. under normoxic conditions to allow repopulation.

The bioreactor may further comprises one or more sensors for determining or monitoring the presence or amount of liver function in the scaffold as it is repopulated with the seeded cells.

Another aspect of the invention provides a bioreactor comprising;
an artificial human liver tissue produced as described above;
an input conduit for the introduction of blood to the artificial human liver tissue; and
an output conduit for the exit of blood from the artificial human liver tissue.

The bioreactor is preferably extracorporeal.

The input and output conduits may be connectable or adapted for connection to the vascular system of an individual, such that the artificial human liver tissue in the bioreactor is perfused with the individuals blood so as to provide liver function to the individual, for example to reduce the accumulation of toxins caused by the loss of endogenous liver function.

The bioreactor may further comprise a tissue chamber for accommodating the artificial human liver tissue.

The artificial human liver tissue may be contained in a suitable culture medium in the bioreactor.

Another aspect of the invention provides decellularisation systems and apparatus adapted to produce a human liver scaffold using a method described above.

A decellularisation system may comprise;
a decellularising device comprising
a tissue chamber for accommodating human liver tissue for decellularisation, and
three or more reagent reservoirs for accommodating decellularisation reagents for introduction to the tissue chamber.

The reagent reservoirs may be operably linked to the tissue chamber, such that reagents from the reservoirs can be introduced to the chamber.

The reagent reservoirs may contain hypotonic reagents, protease and/or DNAase and detergents.

The tissue chamber may contain liver tissue.

In some embodiments, the system may further comprise a sampler adapted to produce liver tissue sections from a human liver sample and load them into the tissue chamber of the decellulariser.

The decellularising device may further comprise one or more pumps for driving decellularisation reagents from the reagent reservoirs into the tissue chamber and optionally removing decellularisation reagents from the tissue chamber.

The chamber may comprise an inlet for introduction of decellularisation reagents and an outlet for removal of reagents.

In some embodiments, human liver tissue in the tissue chamber may be immersed in decellularisation reagent or physiological solutions introduced into the chamber from the reservoir through the inlet. Following exposure to the decellularisation reagent, the reagent may be removed through the outlet and further decellularisation reagent introduced into the chamber, in accordance with a decellularisation regime described herein. The system may further comprise an agitator for agitating human liver tissue immersed in decellularisation reagent in the tissue chamber.

In other embodiments, human liver tissue in the tissue chamber may be perfused in a retrograde direction with decellularisation reagents from the reagent reservoirs. Multiple decellularisation reagents may be perfused through the tissue in series in accordance with a decellularisation regime described herein. The liver tissue may be immersed in physiological solutions or culture medium during perfusion.

The decellularising device may comprise at least one cannulation device for cannulating the liver tissue in the tissue chamber to allow perfusion in a retrograde direction. A suitable cannulation device may comprise size-appropriate hollow tubing for introduction into a vessel, duct, and/or cavity of the human liver tissue. Typically, one or more vessels, ducts, and/or cavities are cannulated in the tissue in the tissue chamber. In some embodiments, the device may comprise an inlet cannulation device for the introduction of decellularisation reagents to the liver tissue and an outlet cannulation device for the egress of decellularisation reagents from the liver tissue.

The decellularising device may further comprise perfusion apparatus for perfusing the liver tissue through the cannula(s). A perfusion apparatus can include a mechanism for moving the decellularisation reagents from the reservoirs through the human liver tissue (e.g., a pump, air pressure, gravity) via the one or more cannulae, as well as tubes, adaptors and/or connectors for perfusing the cannulated liver tissue in the tissue chamber with decellularisation reagents from the reagent reservoirs.

Cannulation and perfusion are well-known techniques in the art.

The decellularising device may be adapted to maintain a sterile environment for the liver tissue in the tissue chamber. Sterility may be maintained during decellularisation using a variety of techniques known in the art, such as controlling and filtering the air flow and/or perfusing with, for example, antibiotics, anti-fungals or other anti-microbials to prevent the growth of unwanted microorganisms. Suitable antimicrobial compounds are well known in the art.

The decellularising device may be adapted to monitor certain perfusion characteristics (e.g., pressure, volume, flow pattern, temperature, gases, pH), mechanical forces (e.g. ventricular wall motion and stress). For example, the system may comprise sensors that monitor the system (e.g., bioreactor) and/or the liver tissue. Sensors may be used to monitor the pressure of a liquid moving through the cannulated liver tissue; the ambient temperature in the system and/or the temperature of the liver tissue; the pH and/or the rate of flow of a liquid moving through the cannulated liver tissue; and/or the biological activity of a recellularising liver tissue. In addition to having sensors for monitoring such features, a system for decellularising and/or recellularising liver tissue may comprise include controls for maintaining or adjusting such features.

Controls may include components such as a thermometer, a thermostat, electrodes, pressure sensors, overflow valves, valves for opening and closing fluid connections to decellularisation reagents and altering rates and directions of flow.

To help ensure stable conditions (e.g., temperature), the chambers, reservoirs and tubing may be water-jacketed.

The system for generating a human liver scaffold may be controlled by a programmable processor. For example, the processor may receive and process information from one or more of the sensors. The processor may transmit information and instructions back to the bioreactor and/or the liver tissue.

The processor may be adapted or programmed to calculate exposure times and perfusion pressures for each decellularisation reagent according to a decellularisation method as described herein for that particular liver tissue, based on the weight and internal resistance of liver tissue. The processor may change the decellularisation reagent and alter the perfusion pressure, via one or more pumps and/or valve controls in the system. The processor may record preload and afterload (the pressure before and after perfusion, respectively) for each decellularisation step and the rate of flow.

The system may be adapted to monitor liver tissue undergoing decellularisation for biological activity. For example the mechanical activity, mechanical pressure, and/or wall stress of the liver tissue may be monitored.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

Abbreviations; SdC Sodium Deoxycholate; PBS/AA PBS+Antibiotic Antimycotic; T/E 0.025% Trypsin/EDTA 0.025%; SDS Sodium Dodecyl Sulfate; TX100 Triton X 100; RT Room Temperature; PAA Paracetic Acid; EtOH Ethanol.

1. Methods 1.1 Human Liver Harvest and Cannulation

Discarded Human Liver Organs (DHLO) unsuitable for liver transplantation were heparinized according to the standard procedure for transplantation. DHLOs are adequately prepared by multiple block subdivision in small non-vascularized liver units of 0.2-1.0 cm (Liver Tissue Cubes, LTC) and/or by segmental or sub-segmental preparation of units provided of vascular-biliary pedicles. The whole human liver or alternatively the left lobe (segments 2-3-4±1), right lobe (segments 5-8) or the left lateral liver (Segments 2-3±1) as well as the Liver Tissue Cubes (LTC) were frozen at −80 C for at least 24 h hours to facilitate cell lysis.

1.2 Perfusion Decellularisation of the Whole Human Liver Left Lobe

First, the whole human liver lobe was thawed overnight in PBS at 4° C. Secondly, the vena cava or the hepatic veins were cannulated to initiate a retrograde perfusion system.

Figure 1:
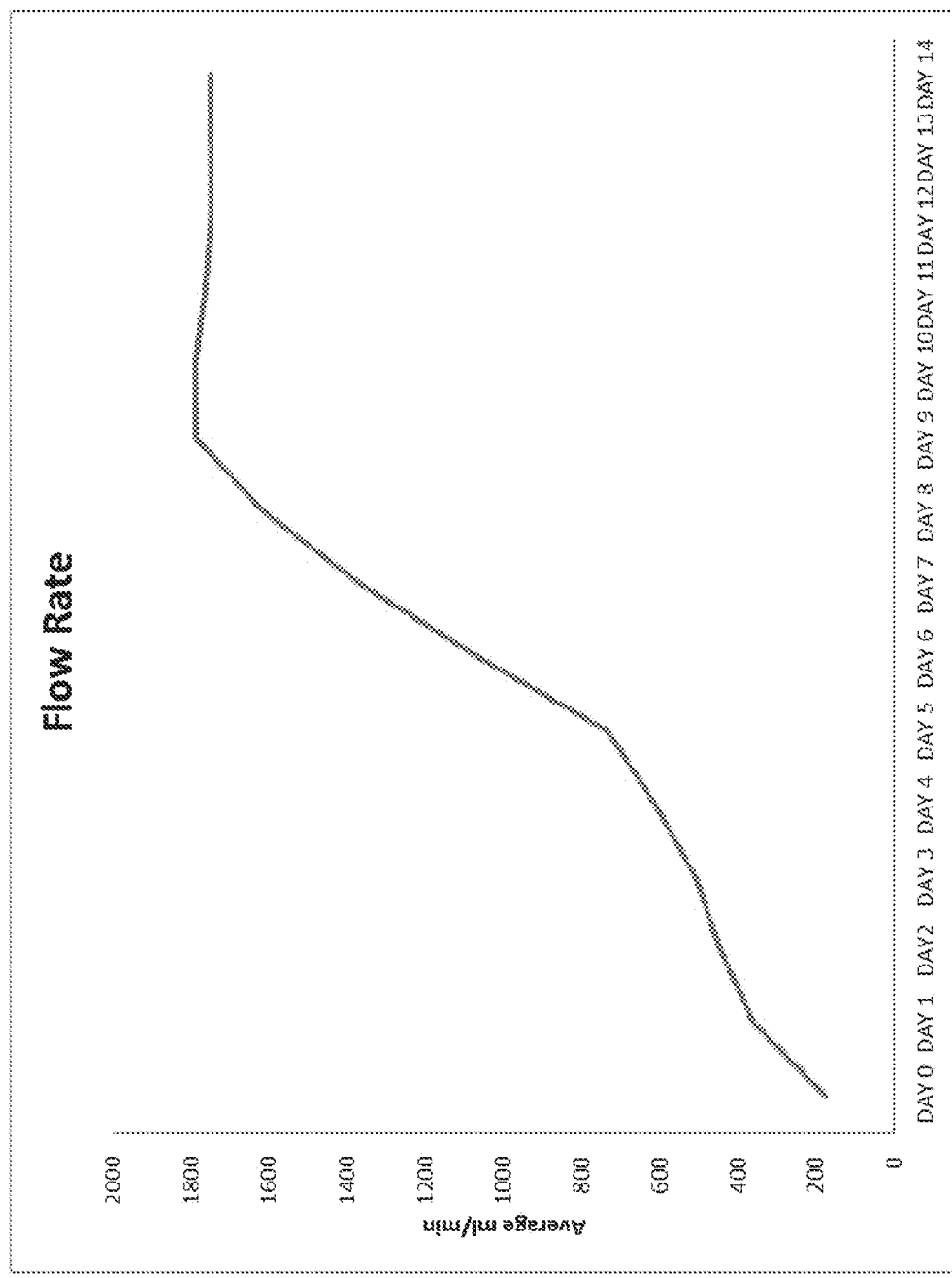
FIG. 1 shows flow rate (in ml/min) relative to the different phases of perfusion over the 14 days of the decellularisation process.
Figure 2:
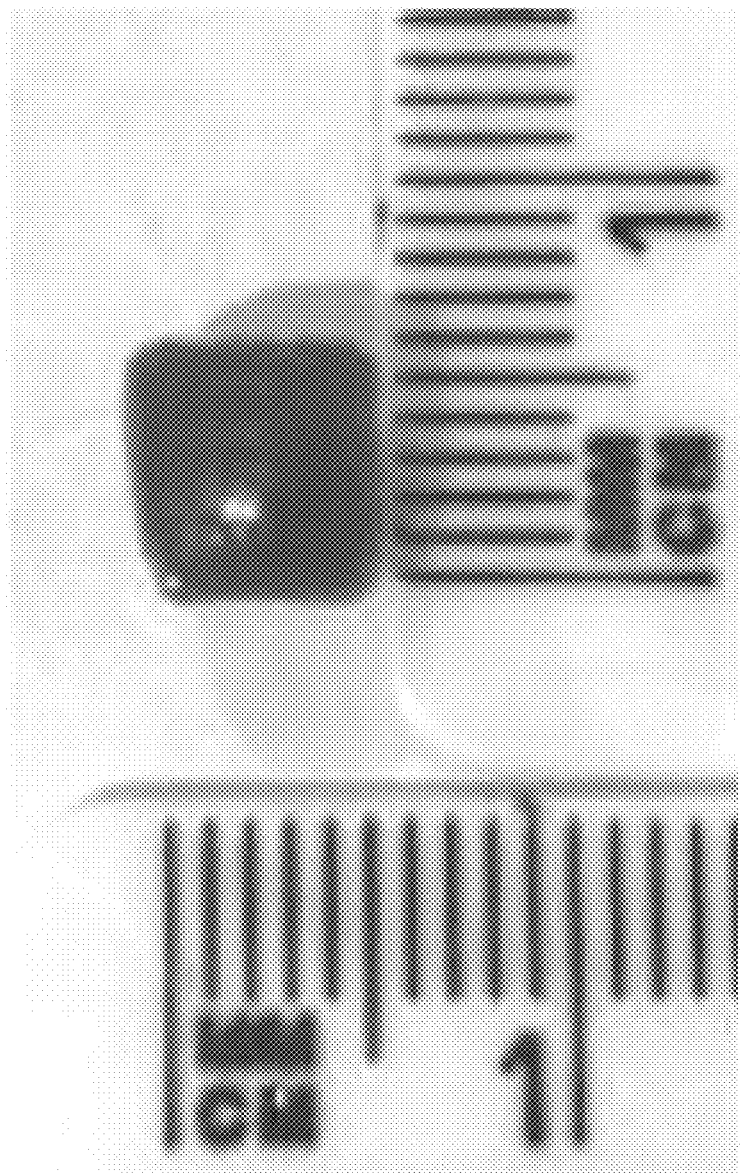
FIG. 2 shows $125=^3$ Liver Tissue Cubes (LTCs) before decellularisation.

Finally, the 5CDFs were applied to achieve full organ decellularisation, as shown in Table 1, 2 and FIG. 1. Two phases of perfusion were adopted a) steeply increasing flow rate to compensate resistance b) stabilization of the flow rate as the decellularisation proceeds. The two phases of flow rate are shown in FIG. 1.

1.3 Agitation Decellularisation of Human LTC

The LTCs were thawed at 37 C for 1-1.5 h. The protocol for the decellularisation of LTCs is shown in Tables 3 to 5.

2. Results

Figure 3:
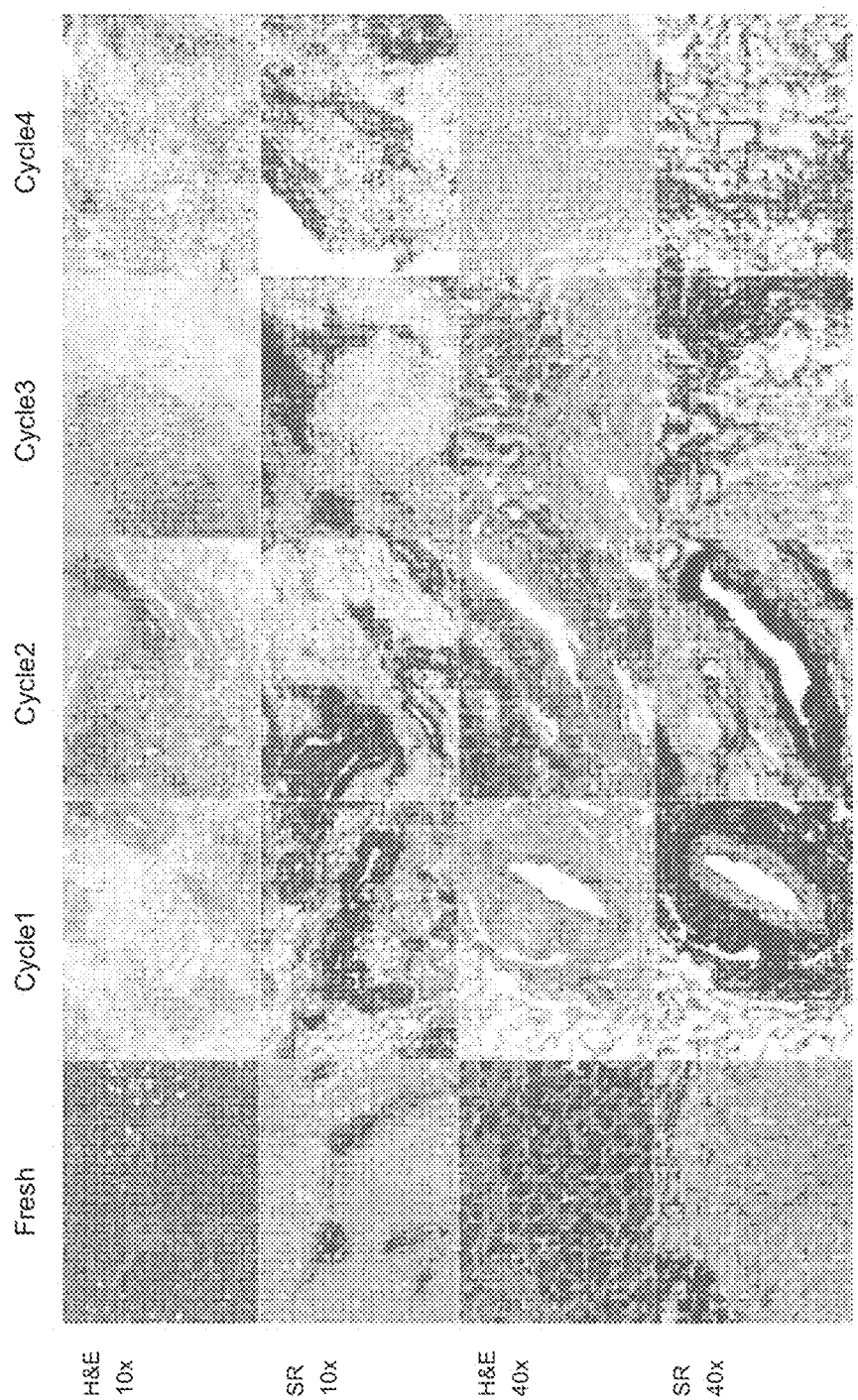
FIG. 3 shows histological comparison of native tissue and decellularised LTCs (dLTCs) after 4 decellularisation cycles. H&E (Haematoxylin and Eosin) staining showed removal of cells after LTCs decellularisation and SR (Sirius Red) staining showed preservation of collagen (red) and removal of cellular materials (yellow).

Native liver tissue and decellularised LTCs (dLTCs) were compared histologically after 4 decellularisation cycles. The decellularisation cycles were found to have removed cells and cellular material from the LTCs, whilst preserving collagen (FIG. 3).

Figure 4:
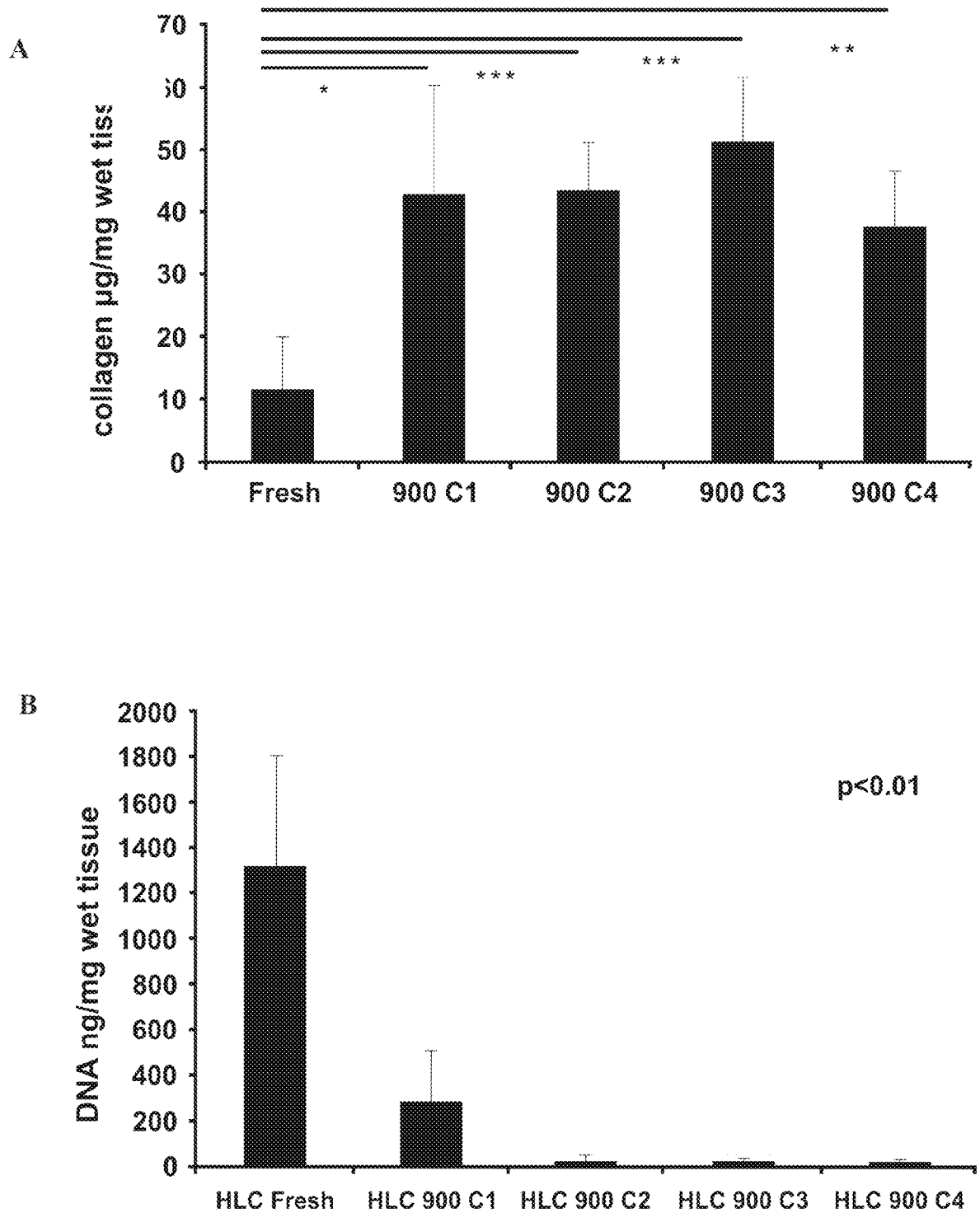
FIG. 4 shows quantitative measurement of Collagen (A) and DNA (B) after decellularisation. Collagen quantification following different agitation speeds (900C1-900C4) demonstrated a preservation of the amount of collagen when compared to fresh tissue. Decellularisation was efficient with a marked decrease in DNA content (p<0.01) already after 1 treatment cycle (B).

Collagen and DNA were quantified in the dLTCs after decellularisation. The amount of collagen in the dLTCs was found to be preserved at different agitation speeds when compared to fresh tissue (900C1-900C4) (FIG. 4A). Decellularisation was efficient with a marked decrease in DNA content (p<0.01) after only 1 treatment cycle (FIG. 4B).

Figure 5:
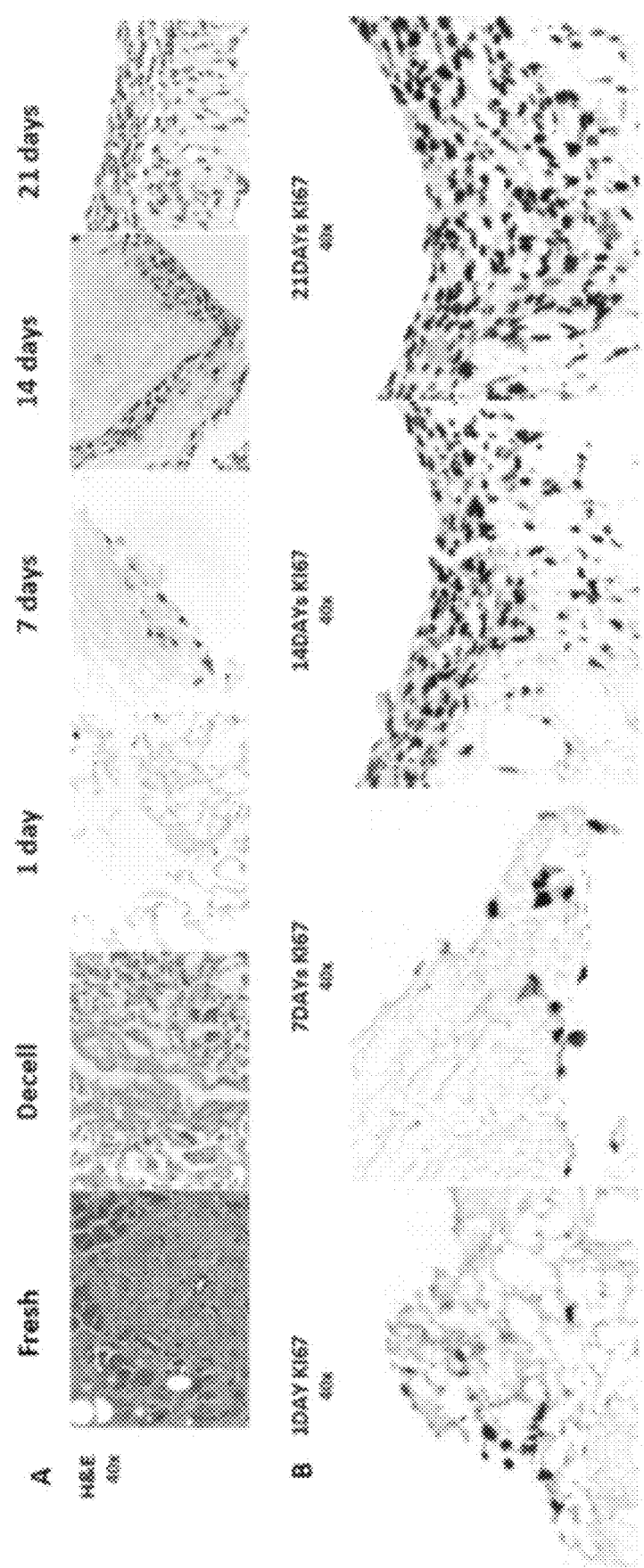
FIG. 5 shows repopulation of human liver scaffolds with the human hepatic stellate cell line LX2. (A) H&E staining demonstrates progressive LX2 cell migration into the LTC scaffold when comparing day 1 with 21 days after recellularisation. (B) The process of repopulation is characterized by marked cell proliferation as detected with an immunostaining for the proliferation marker Ki67.
Figure 6:
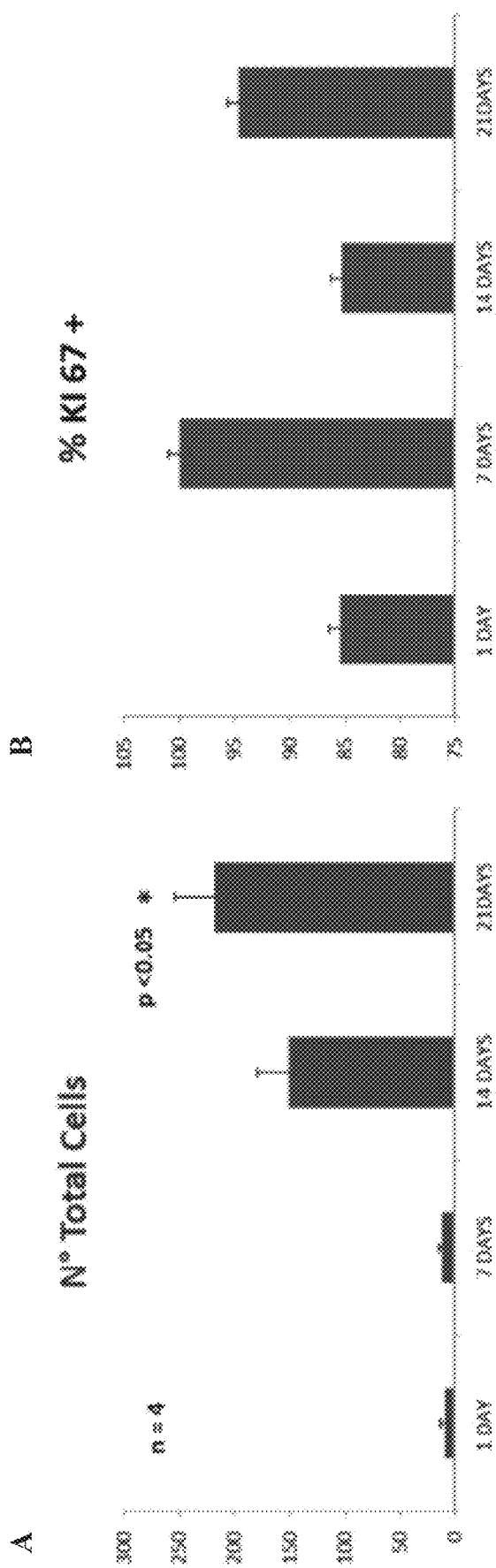
FIG. 6 shows an increase in the total cell count after 14 days of repopulation with LX2. Importantly, the total cell count in human liver scaffolds significantly increased between 14 and 21 days (A). KI67 immunohistochemistry shows that more than 85% of the cells were proliferating at all different time points (B).

Decellularised human LTCs were repopulated with the human hepatic stellate cell line LX2. The LX2 cells were found to progressively migrate into the LTC scaffold over 21 days after recellularisation (FIG. 5A). The total cell count in the human liver scaffolds was found to increase after 14 days of repopulation with LX2 and significantly increased between 14 and 21 days (FIG. 6A). Immunostaining for the proliferation marker Ki67 showed that the process of repopulation is characterized by marked cell proliferation (FIG. 5B) and at all different time points, more than 85% of the cells were proliferating (FIG. 6B).

Figure 7:
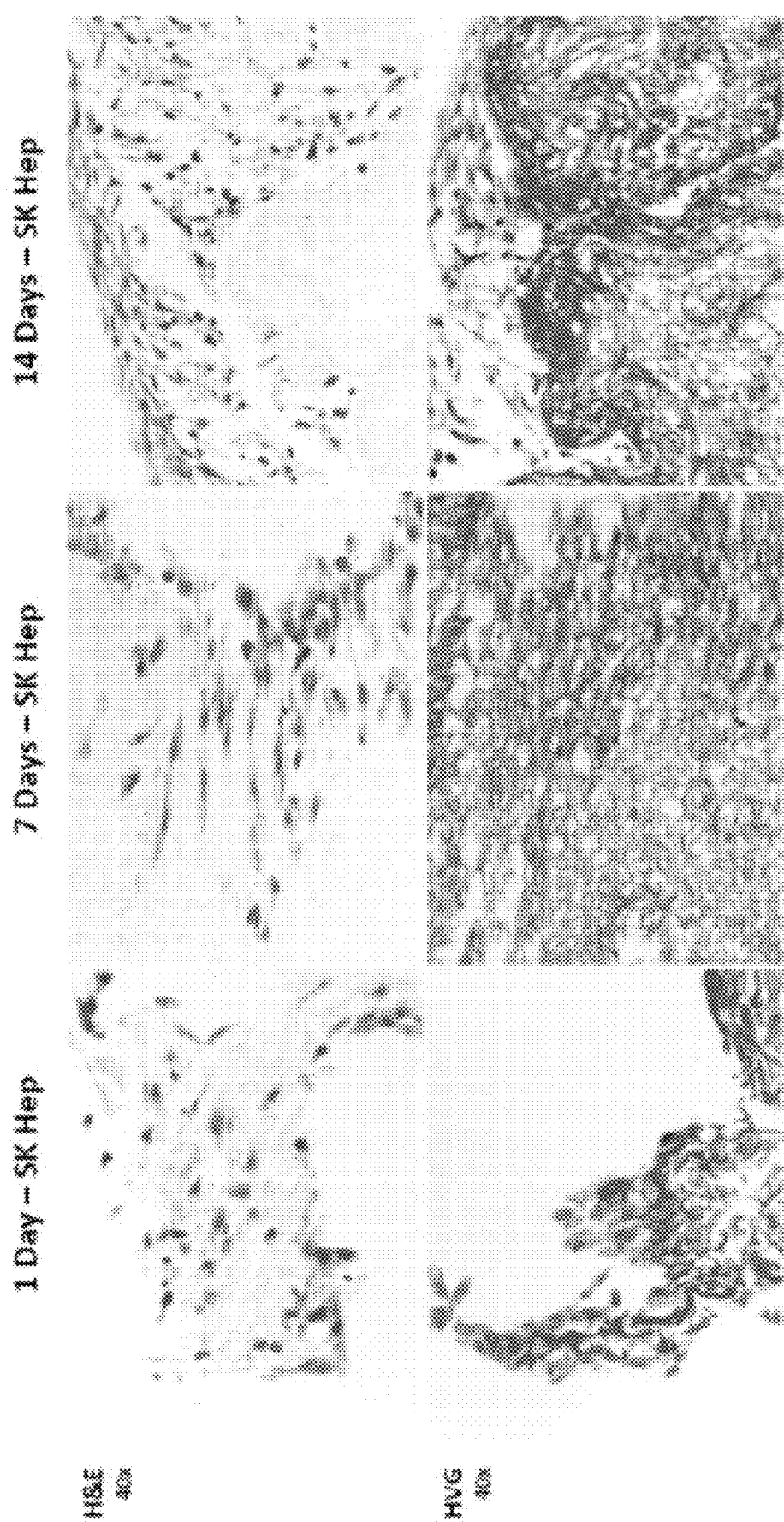
FIG. 7 shows repopulation of decellularised human liver scaffolds with the human hepatocellular carcinoma cell line SK-Hep. H&E and HVG (Haematoxylin Van Gieson) staining demonstrates cell attachment after 1 day of bioengineering and progressive cell migration into the human liver scaffold when comparing day 1 with day 14 after recellularisation.
Figure 8:
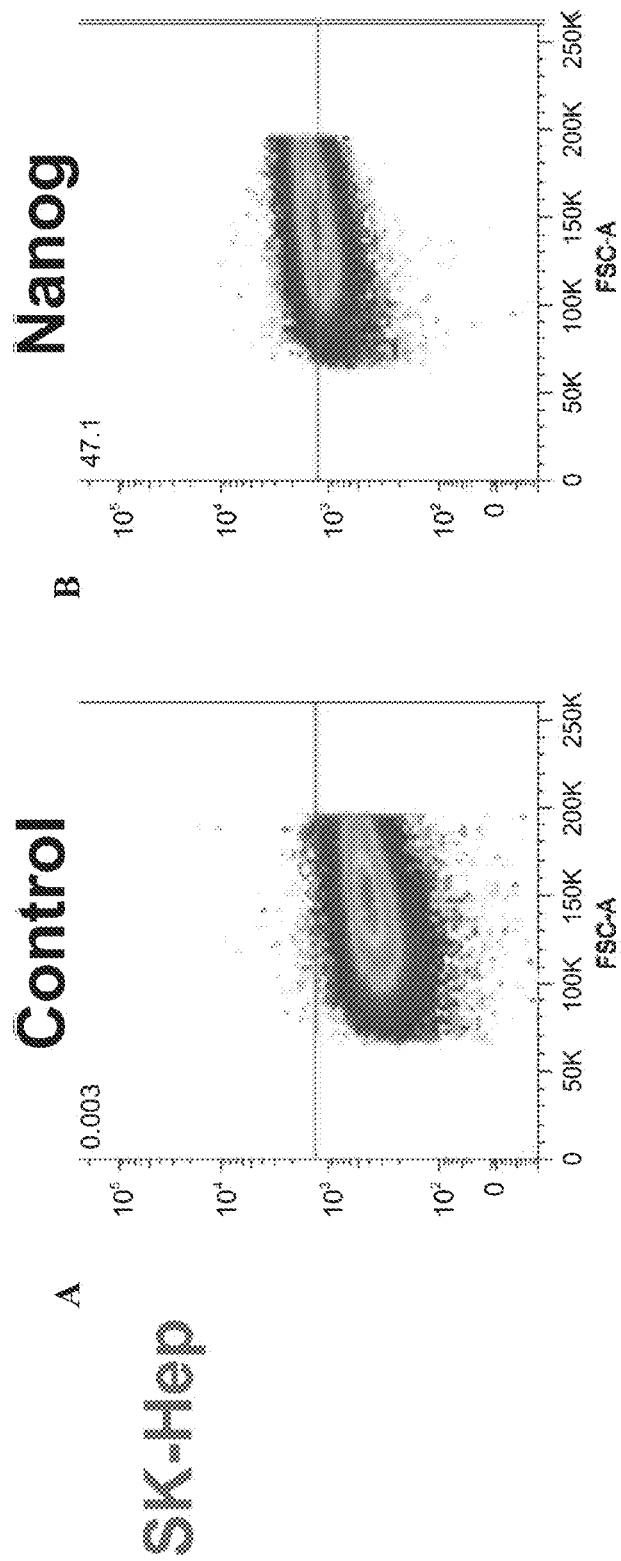
FIG. 8 shows FACS staining of SK-Hep with anti-human Nanog (B) and Isotype control (A).
Figure 9:
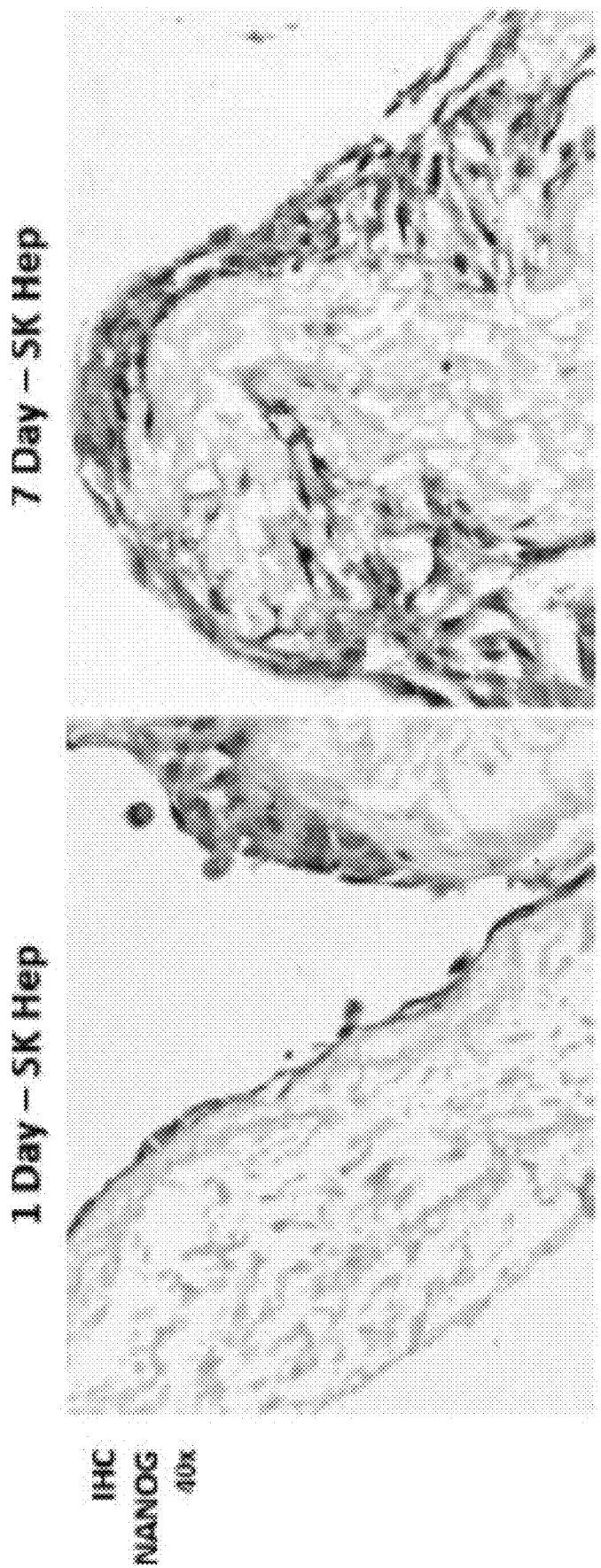
FIG. 9 shows repopulation of decellularised human liver scaffolds with human hepatocellular carcinoma cell line SK-Hep after 1 and 7 days. Nanog expression was analysed by immunohistochemistry. It is evident that the cells attached to the ECM at day 1 and the cells which migrating within the scaffold at day 7 are Nanog positive cells.
Figure 10:
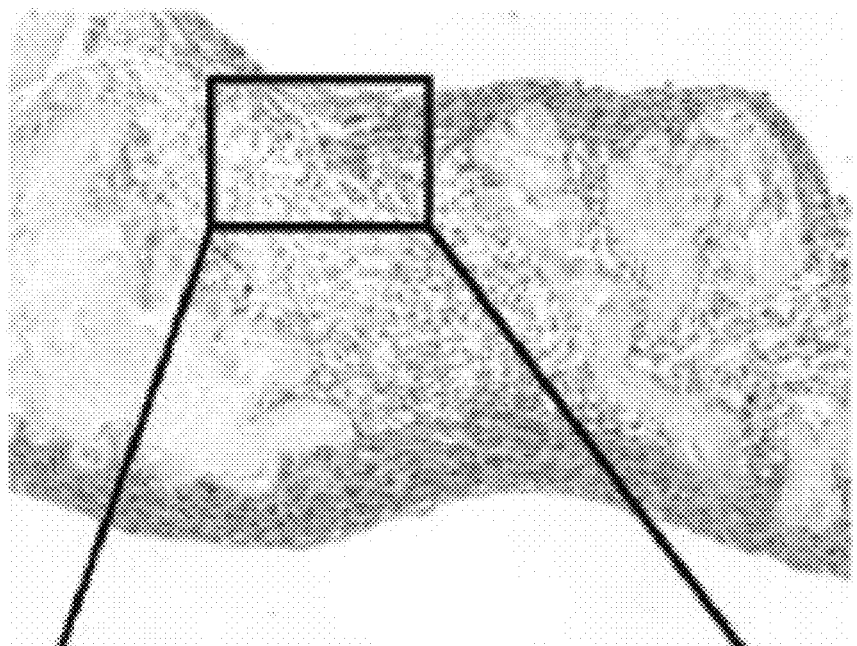
FIG. 10 shows repopulation of decellularised human liver scaffolds with human hepatocellular carcinoma cell line SK-Hep after 14 days. Nanog expression was analysed by immunohistochemistry (Brown) and cells were counterstained with Hematoxilin (Blue). The process of repopulation after 14 days is characterized by both Nanog positive and Nanog negative cells (B). It is remarkable that at this stage Nanog positive cells surround the repopulated scaffold (A) with features resembling the development of human hepatocellular carcinoma.
Figure 10:
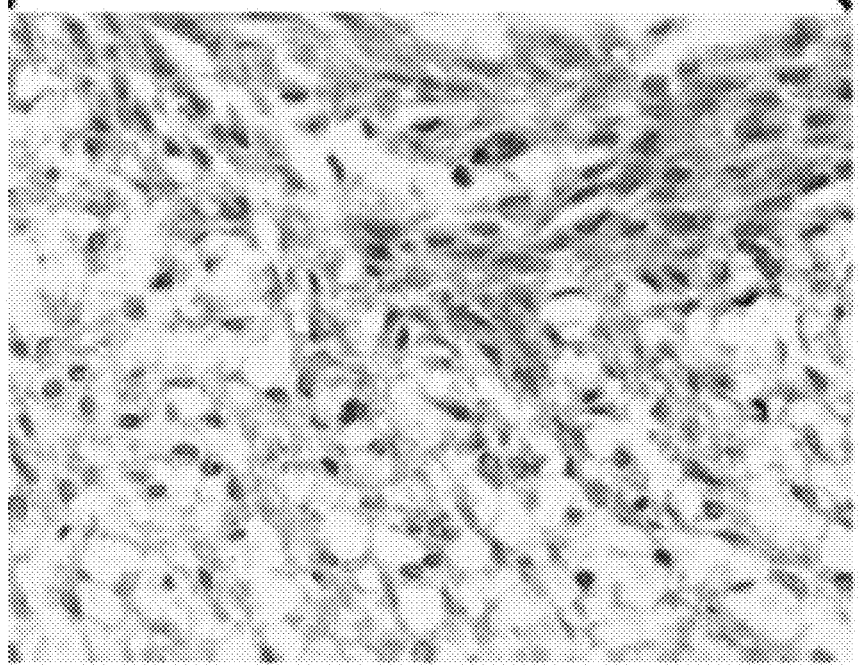

Decellularised human liver scaffolds were repopulated with the human hepatocellular carcinoma cell line SK-Hep. Cell attachment was observed after 1 day of bioengineering and the SK-Hep cells progressively migrated into the human liver scaffold in the 14 days after recellularisation (FIG. 7). Cells attached to the ECM at day 1 and the cells which migrating within the scaffold at day 7 were shown to be Nanog positive cells (FIGS. 8 and 9). The process of repopulation after 14 days was characterized by both Nanog positive and Nanog negative cells (FIG. 10). Remarkably, after 14 days, Nanog positive cells were found to surround the repopulated scaffold with features resembling the development of human hepatocellular carcinoma (FIG. 10A).

Figure 11:
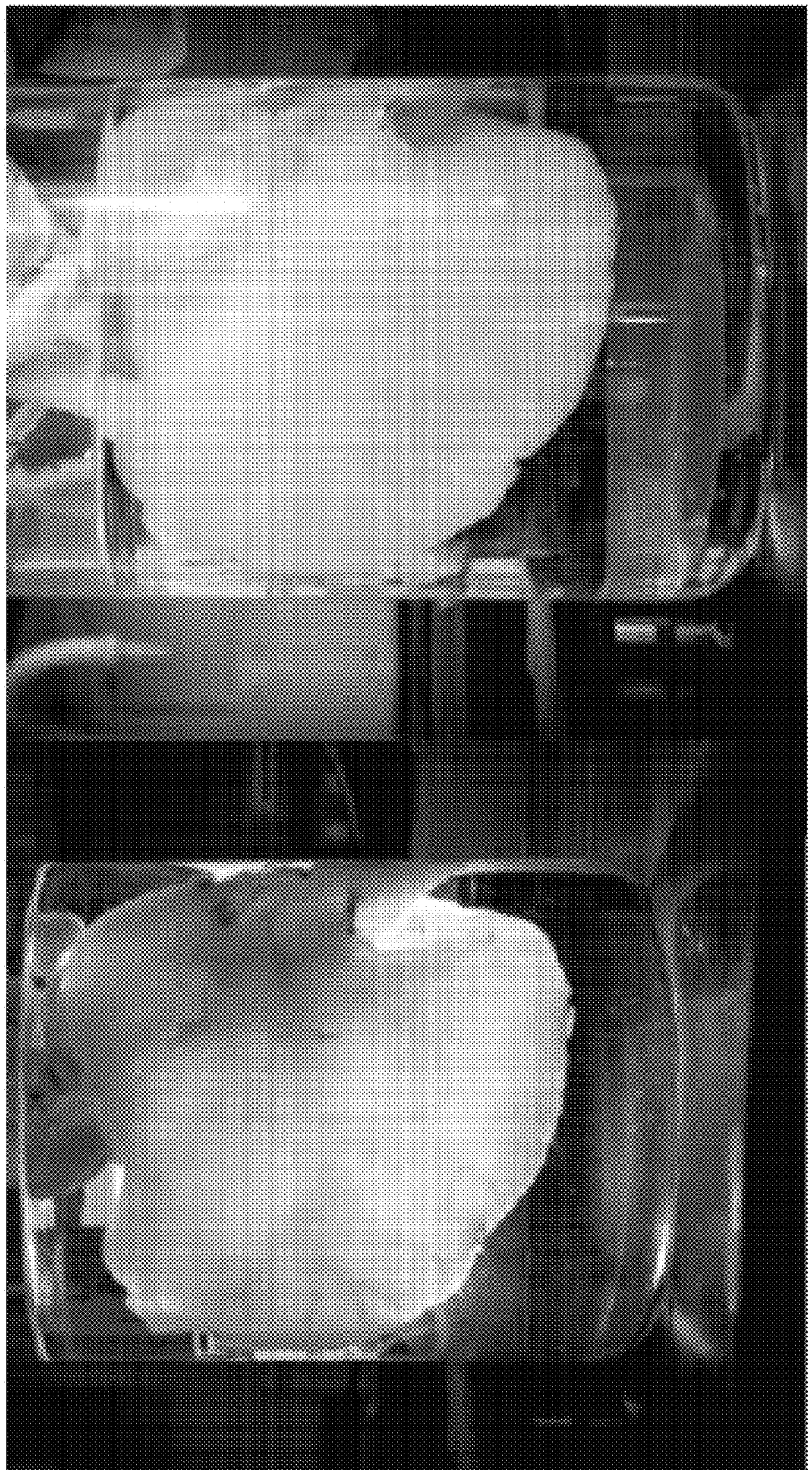
FIG. 11 shows the macroscopic appearance of the decellularised human liver left lobe using two different light backgrounds to highlight the preservation of the vascular tree.
Figure 12:
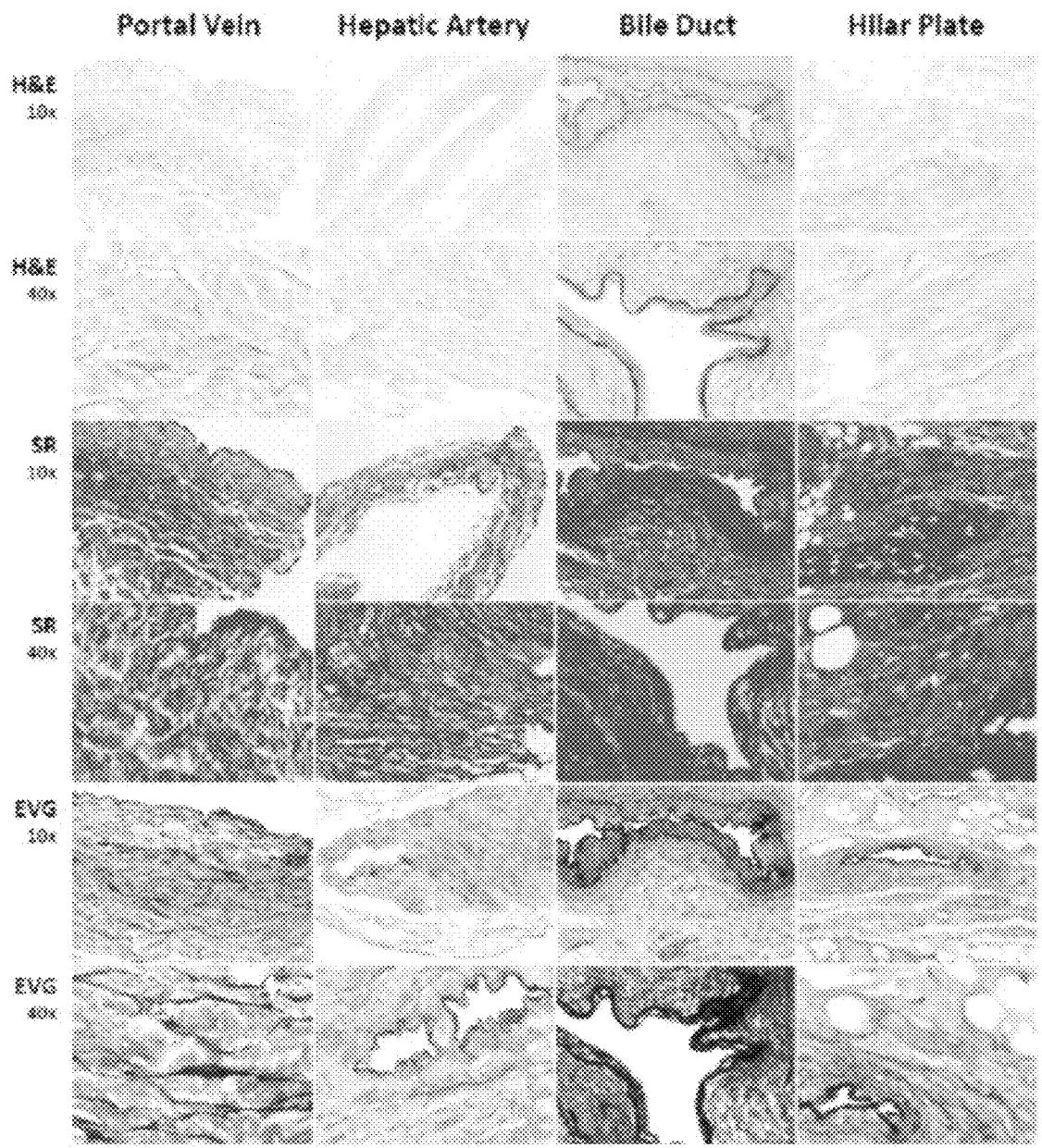
FIG. 12 shows histological sections of the decellularised vascular (portal vein, hepatic artery and hilar plate) and biliary tree. H&E shows absence of cells in the decellularised tissues. SR and EVG stainings show collagen (red) and elastin (blue) preservation, respectively.

The vascular tree of the human liver left lobe was found to be preserved observed following decellularisation (FIG. 11). Cells were found to be absent from the decellularised tissues whilst collagen and elastin were preserved (FIG. 12).

Figure 13:
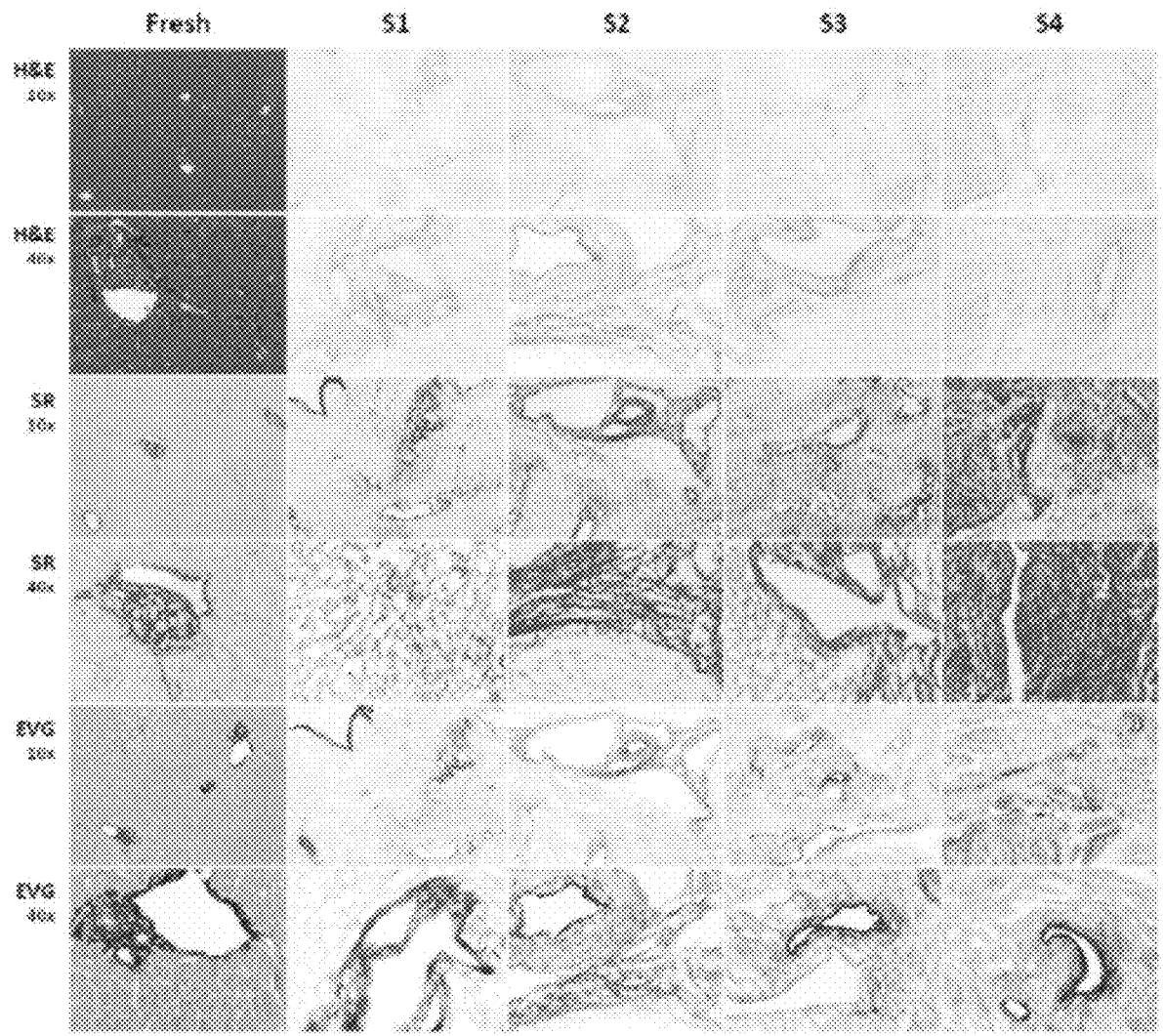
FIG. 13 shows histological comparison of fresh liver tissue and the decellularised human liver left lobe segments (S1, S2, S3 and S4). H&E staining showed removal of cells after decellularisation and SR and EVG (Elastic Van Gieson) stainings show collagen (red) and elastin (blue) preservation, respectively.

Comparison of fresh liver tissue and the decellularised human liver left lobe segments (S1, S2, S3 and S4) confirmed the removal of cells after decellularisation and the preservation of collagen and elastin (FIG. 13).

Figure 14:
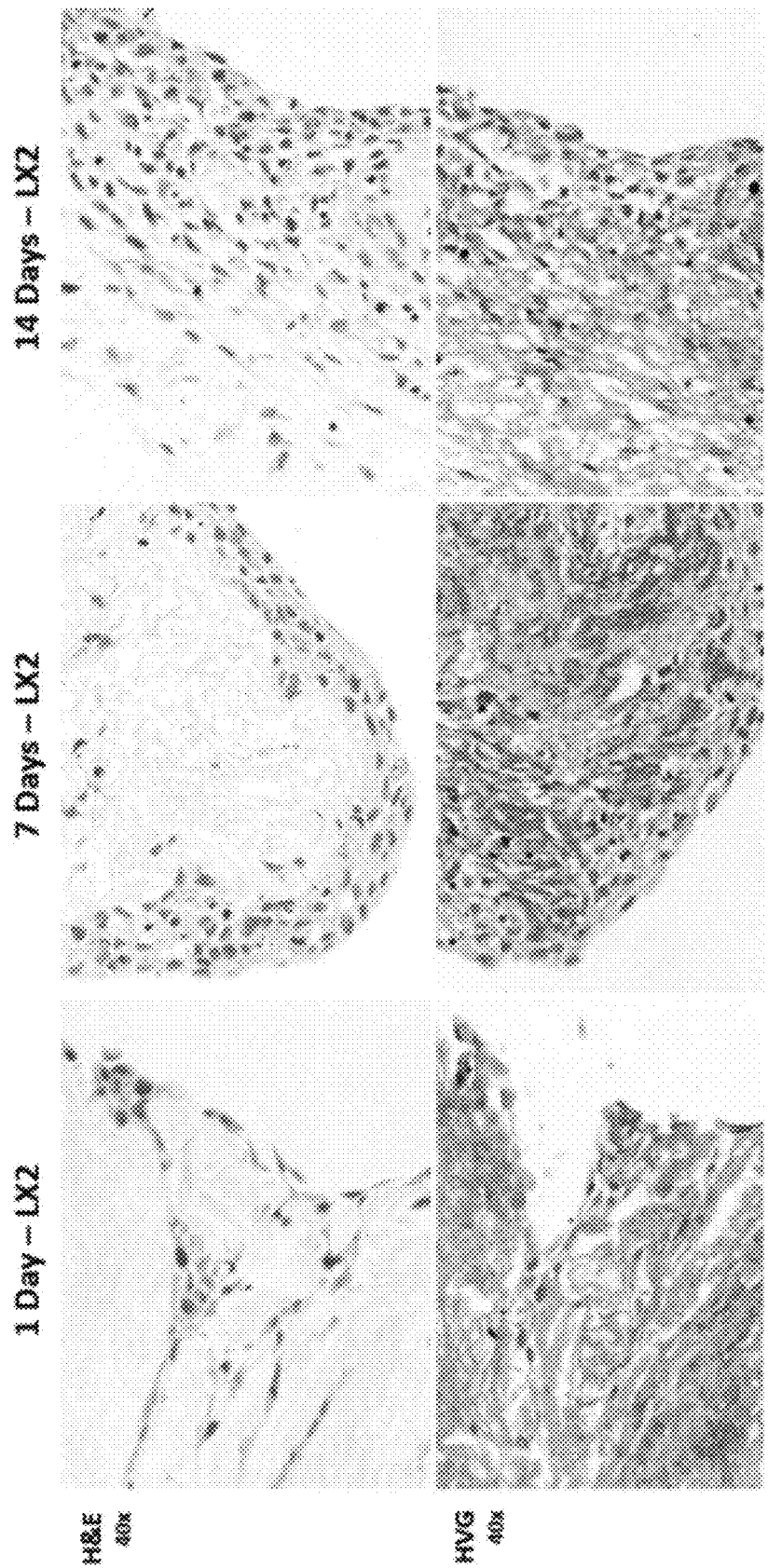
FIG. 14 shows repopulation of human liver scaffolds with the human hepatic stellate cell line LX2. H&E and HVG stainings demonstrate cell attachment after 1 day of bioengineering and progressive cell migration into the human liver scaffold when comparing day 1 with day 14 after recellularisation.

Decellularised human liver left lobe segments were repopulated with the human hepatic stellate cell line LX2. The LX1 cells were found to attach to the decellularised scaffold after 1 day and to progressively migration into the scaffold over 14 days (FIG. 14).

Figure 15:
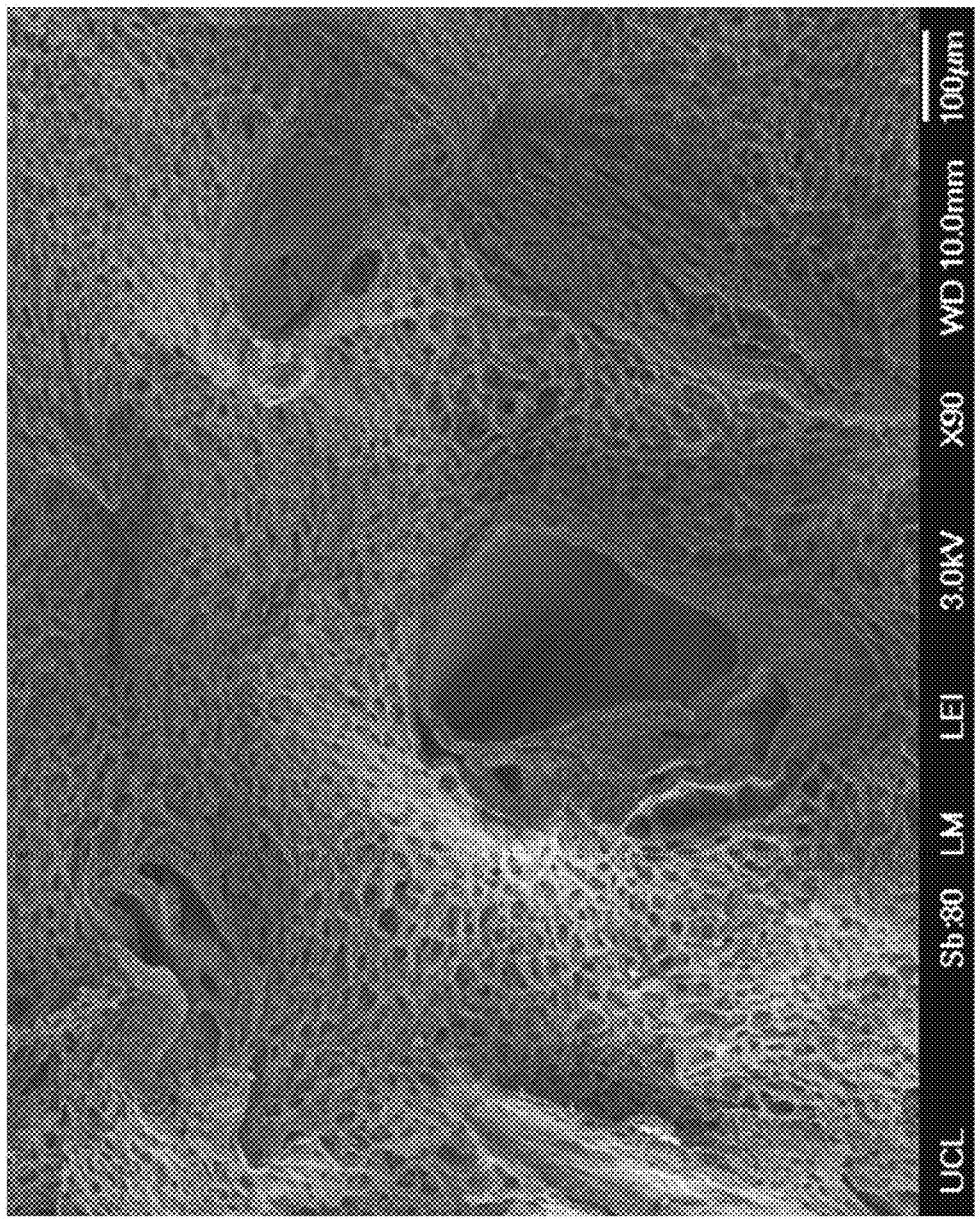
FIG. 15 shows a low magnification (90×) SEM image including a portal tract surrounded by a typical lobular structure.
Figure 16:
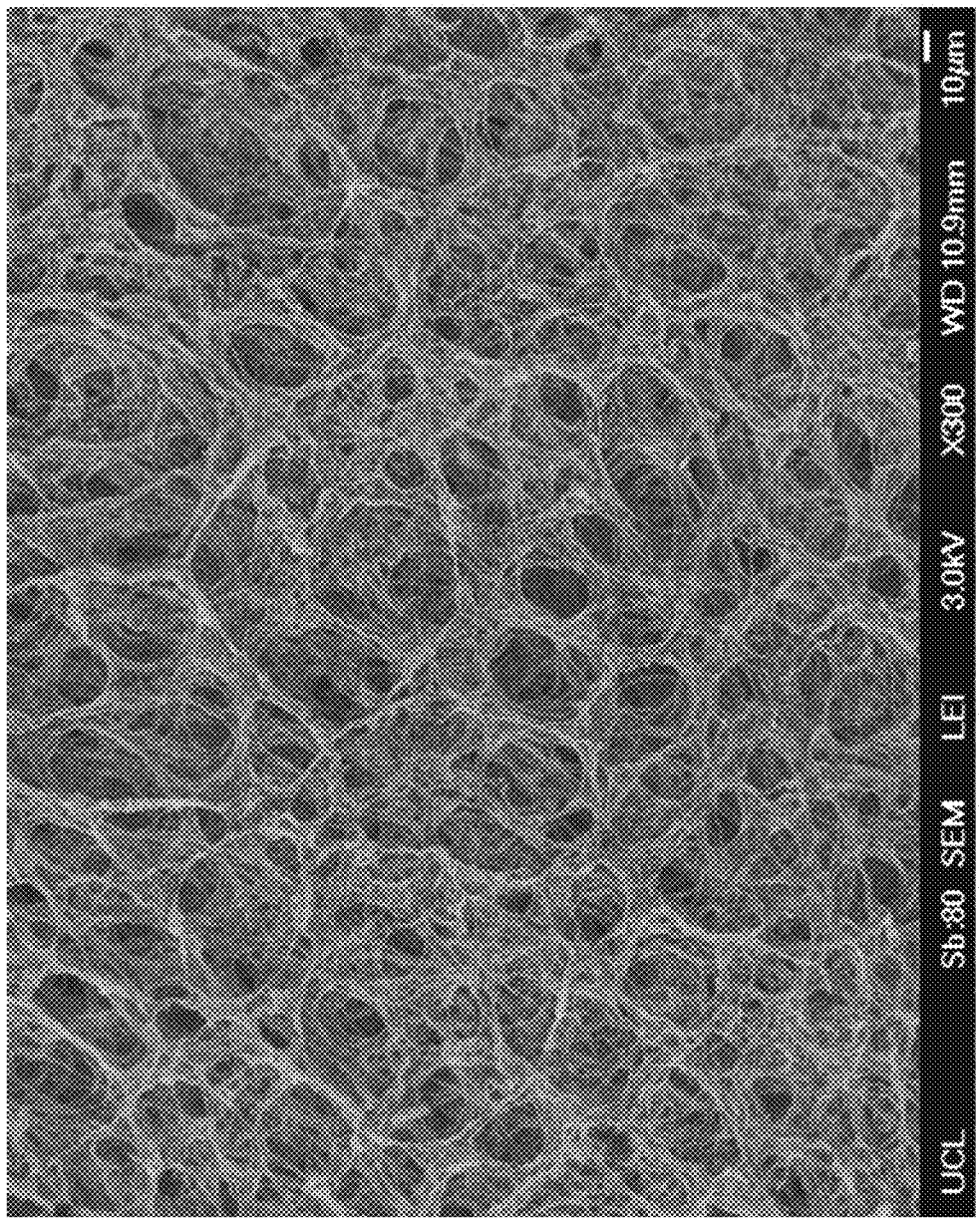
FIG. 16 shows a 300×SEM image confirming scaffold acellularity and clearly defining spaces once occupied by hepatocytes (i.e. hepatocyte-free spaces).
Figure 17:
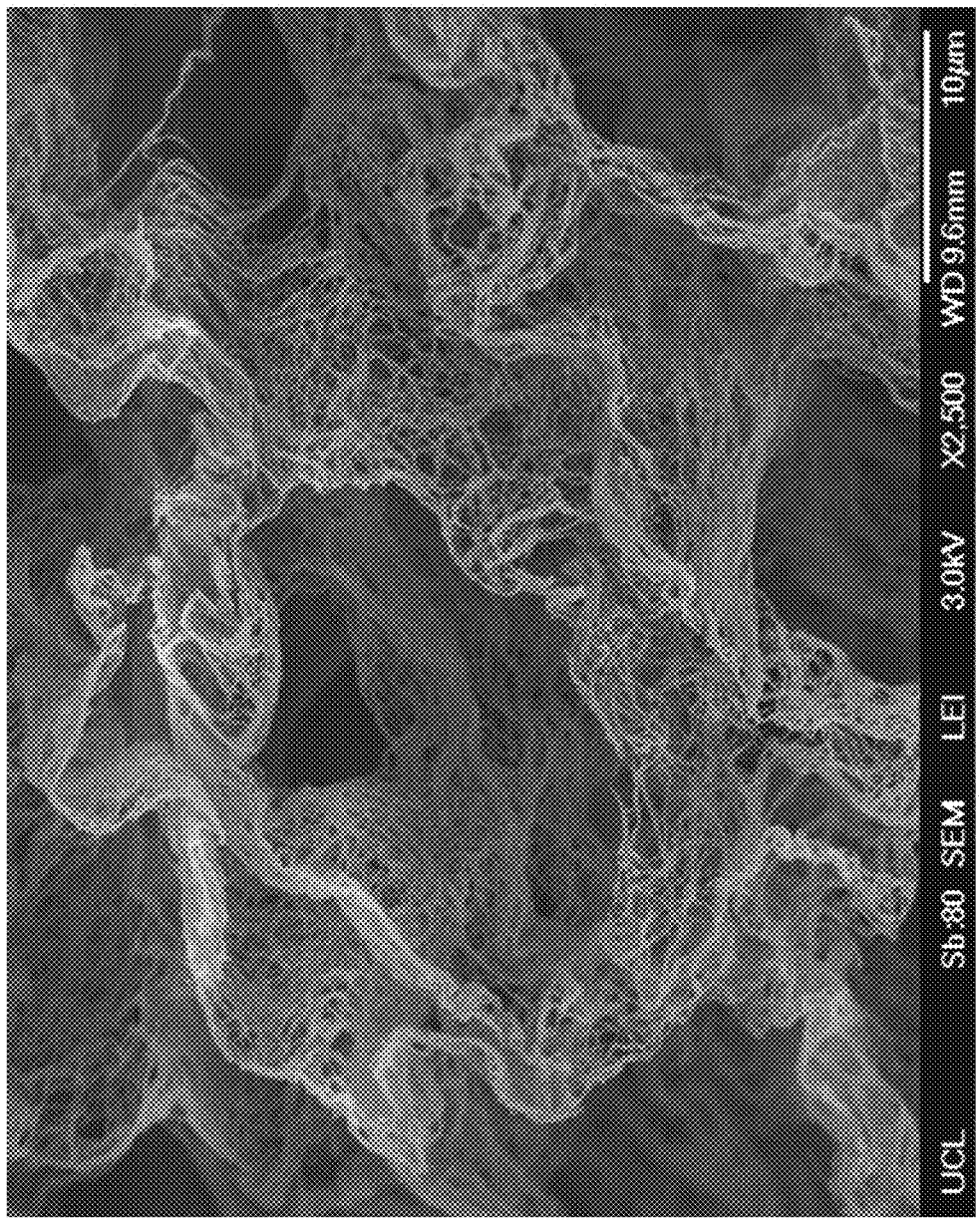
FIG. 17 shows a high magnification (2500×) SEM image demonstrating an exceptionally preserved three-dimensional meshwork of connective tissue fibres structuring the hepatocyte-free spaces.

Decellularised human liver scaffolds were analysed by scanning electron microscopy. The SEM images confirmed scaffold acellularity and showed the presence of clearly defined spaces once occupied by hepatocytes (i.e. hepatocyte-free spaces). The three-dimensional meshwork of connective tissue fibres structuring the hepatocyte-free spaces, as well as portal tracts and lobular structure, were found to be an exceptionally preserved (FIGS. 15-17).

TABLE 1

| DAY | Steps and Reagents |
| --- | --- |
| DAY −1 | Thaw the liver o.n. at 4° C. |
| DAY 0 | dH2O |
|  | 0.025% Trypsin/EDTA |
| DAY 1 | dH2O |
|  | 0.01% SDS |
|  | 0.1% SDS |
|  | 1% SDS |
| DAY 2 | dH2O |
|  | 0.025% Trypsin/EDTA |
|  | 1% SDS |
| DAY 3 | dH2O |
|  | 3% TX100 |
| DAY 4 | dH2O |
|  | 3% TX100 |
| DAY 5 | dH2O |
|  | 3% TX100 |
| DAY 6 | dH2O |
|  | 3% TX100 |
| DAY 7 | dH2O |
|  | 0.025% Trypsin/EDTA |
| DAY 8 | dH2O |
|  | 1% SDS |
| DAY 9 | dH2O |
|  | 1% SDS |
| DAY 10 | dH2O |
|  | 1% SDS |
| DAY 11 | dH2O |
|  | 1% SDS |
| DAY 12 | dH2O |
|  | 1% SDS |
| DAY 13 | dH2O |
|  | PBS/Antib-Antimic 5% |
|  | 3% TX100 |
| DAY 14 | dH2O |
|  | PBS |
|  | PBS/Antib-Antimic 5% |
|  | dH2O |
|  | 0.1% PAA/4% EtOH |
|  | PBS |

TABLE 2

| DAY 0 | DAY 1 | DAY 2 | DAY 3 | DAY 4 | DAY 5 | DAY 6 | DAY 7 | DAY 8 | DAY 9 | DAY 10 | DAY 11 | DAY 12 | DAY 13 | DAY 14 |
|---|---|---|---|---|---|---|---|---|---|---|---|---|---|---|
| 100 | 300 | 425 | 475 | 550 | 675 | 850 | 1300 | 1500 | 1750 | 1750 | 1800 | 1750 | 1750 | 1750 |
| 150 | 350 | 450 | 500 | 600 | 700 | 1000 | 1350 | 1550 | 1755 | 1800 | 1750 | 1750 | 1750 | 1750 |
| 200 | 375 | 450 | 525 | 650 | 750 | 1200 | 1400 | 1700 | 1850 | 1800 | 1750 | 1750 | 1750 | 1750 |
| 250 | 400 | 450 | 525 | 650 | 800 | 1200 | 1400 | 1700 | 1900 | 1800 | 1750 | 1750 | 1750 | 1750 |
|  |  |  |  |  |  |  |  |  | 1700 |  |  |  |  |  |
|  |  |  |  |  |  |  |  |  | 1750 |  |  |  |  |  |

TABLE 3

| Time | Reagents | Temperature | rpm |
|---|---|---|---|
| 24 h | dH20 | 4° C. | 900 |
| 4-6 h | SdC 4% | RT | 900 |
| 5 min | PBS | RT | 900 |
| 3 h | Dnase | RT | 900 |
| 5 min | PBS/AA | RT | 900 |

TABLE 4

| Time | Reagents | Temperature | rpm |
|---|---|---|---|
| 12-36 h | dH20 | 4° C. | 100-1000 |
| 4-12 h | SdC 4% | RT | 100-1000 |
| 5-30 min | PBS | RT | 100-1000 |
| 3 h | Dnase | RT | 100-1000 |
| 5-30 min | PBS/AA | RT | 100-1000 |

TABLE 5

| Time | Reagents | Temperature | rpm |
|---|---|---|---|
| 15-30 min | dH20 | RT | 100-1000 |
| 12-36 h | T/E 0.025% | RT | 100-1000 |
| 12-72 h | SDS 0.01-1% | RT | 100-1000 |
| 12-72 h | TX100 3% | RT | 100-1000 |
| 5-30 min | PBS/AA | RT | 100-1000 |

TABLE 6

|  | Reagents (1.2 ml) | Overall Time | Agitating System | Speed (rpm) | Calculated G-force (g) |
|---|---|---|---|---|---|
| OS-1 | 1. Deionised water, 24 hrs<br>2. PBS 1%, 5 mins<br>3. SDC 4%, 5.5 hrs<br>4. PBS 1%, 5 mins<br>5. DNase solution, 3 hrs<br>6. PBS 1%, 5 mins<br>7. Repeated steps 1-6 a total of 4 and 8 times | 8 days<br>16 days | Labnet - Orbit™ M60 microtube shaker | 900 | 0.432 |
| OS-D | 1. Alternate between deionised water and dextrose solution, 1 hr each for 8 hrs<br>2. Deionisd water, 16 hrs<br>3. PBS 1%, 5 mins<br>4. SDC 4%, 5.5 hrs<br>5. PBS 1%, 5 mins<br>6. DNase solution, 3 hrs<br>7. PBS 1%, 5 mins<br>8. Repeated steps 1-7 a total of 4 times | 8 days | Labnet Orbit™ M60 microtube shaker | 900 | 0.432 |
| MS-1 | 1. Deionised water, 24 hrs<br>2. PBS 1%, 5 mins<br>3. SDC 4%, 5.5 hrs<br>4. PBS 1%, 5 mins<br>5. DNase solution, 3 hrs<br>6. PBS 1%, 5 mins<br>7. Repeated steps 1-6 a total of 4 times | 8 days | Magnetic Stirrer | 300-400 | 5.0-8.9 |
| MS-S | 1. Deionised water, 24 hrs<br>2. PBS 1%, 5 mins<br>3. SDC 4%, 5.5 hrs<br>4. PBS 1%, 5 mins<br>5. DNase solution, 3 hrs<br>6. PBS 1%, 5 mins<br>7. Saline Solution 9%, 14.5 hrs<br>8. Repeated steps 1-7 a total of 4 times | 8 days | Magnetic Stirrer | 300-400 | 5.0-8.9 |

The invention claimed is:
1. A method of producing a decellularized human liver scaffold comprising
   (i) providing healthy or pathological human liver tissue comprising a whole liver or a functional unit thereof,
   (ii) mechanically damaging the cells in the tissue,
   (iii) subjecting the cells in the tissue to osmotic stress by exposing the tissue to a hypotonic reagent or hypertonic reagent,
   (iv) exposing the tissue to a protease and/or DNAase, and
   (v) exposing the tissue to a detergent, and
   (vi) repeating steps (iii) to (v) in the following sequence by perfusion through the liver tissue: (iii), (iv), (iii), (iv), (v), [(iii), (v)]$_n$, optionally [(iii), or (iv)], [(iii), (v)]$_n$, where n is independently 1 to 25;
thereby producing a decellularized human liver scaffold, wherein the human liver tissue is subjected to flow shear stress generated by perfusing the human liver tissue in a retrograde direction with the hypotonic reagent, hypertonic reagent, protease and/or DNAase, and detergent during steps (iii) to (vi) at a perfusion rate which increases from an initial value of 0.1-1.99 ml/min/gram of tissue and stabilizes to a target value of 2-20 ml/min/gram of tissue.

2. A method according to claim 1 wherein the cells are mechanically damaged by subjecting the tissue to one or more rounds of freezing and thawing, or by subjecting the tissue to high intensity focused ultrasound (HIFU) or sonication.

3. A method according to claim 1 wherein the hypotonic agent is deionised water.

4. A method according to claim 1 wherein the tissue is exposed to a trypsin or pronase in step (iv).

5. A method according to claim 1 wherein the detergent is an anionic detergent.

6. A method according to claim 5 wherein the anionic detergent is sodium dodecyl sulfate (SDS) or sodium deoxycholate (SdC).

7. A method according to claim 1, wherein the detergent is a non-ionic detergent, and is polyethylene glycol p-(1, 1, 3, 3-tetramethylbutyl)-phenyl ether (Triton X100™).

8. A method according to claim 1 wherein the liver tissue is subjected to a perfusion regime as set forth below:

| DAY | Steps and Reagents |
|---|---|
| DAY −1 | Thaw the liver o.n. at 4° C. |
| DAY 0 | dH2O |
|  | 0.025% Trypsin/EDTA |
| DAY 1 | dH2O |
|  | 0.01% SDS |
|  | 0.1% SDS |
|  | 1% SDS |
| DAY 2 | dH2O |
|  | 0.025% Trypsin/EDTA |
|  | 1% SDS |
| DAY 3 | dH2O |
|  | 3% TX100 |
| DAY 4 | dH2O |
|  | 3% TX100 |
| DAY 5 | dH2O |
|  | 3% TX100 |
| DAY 6 | dH2O |
|  | 3% TX100 |
| DAY 7 | dH2O |
|  | 0.025% Trypsin/EDTA |
| DAY 8 | dH2O |
|  | 1% SDS |
| DAY 9 | dH2O |
|  | 1% SDS |
| DAY 10 | dH2O |
|  | 1% SDS |
| DAY 11 | dH2O |
|  | 1% SDS |
| DAY 12 | dH2O |
|  | 1% SDS |
| DAY 13 | dH2O |
|  | PBS/Antib-Antimic 5% |
|  | 3% TX100 |
| DAY 14 | dH2O |
|  | PBS |
|  | PBS/Antib-Antimic 5% |
|  | dH2O |
|  | 0.1% PAA/4% EtOH |
|  | PBS. |

9. A method according to claim 1 comprising sterilising the scaffold following decellularisation.

10. A method according to claim 1 comprising re-populating the decellularized human liver scaffold with cells to produce artificial liver tissue.

11. A method according to claim 10 wherein the cells are selected from the group consisting of human primary and cell line liver cells, human primary hepatocytes, human endothelial cells, human induced pluripotent stem cells (iPSCs) or cells derived from patient-specific iPSCs, human embryonic stem cells (hESCs), human mesenchymal stem cells (hMSCs), human fetal stem cells, human cancer cells and human endothelial progenitor cells (EPCs).

12. A method according to claim 1, further comprising:
providing a sample of the decellularized human liver scaffold, wherein the human liver tissue was obtained from a healthy or pathological human liver, and
determining the presence and amount of one or more liver scaffold proteins in the sample.

* * * * *

UNITED STATES PATENT AND TRADEMARK OFFICE
CERTIFICATE OF CORRECTION

PATENT NO. : 10,688,221 B2
APPLICATION NO. : 15/316064
DATED : June 23, 2020
INVENTOR(S) : Giuseppe Mazza et al.

Page 1 of 1

It is certified that error appears in the above-identified patent and that said Letters Patent is hereby corrected as shown below:

On the Title Page

Assignee item (73) should read --UCL BUSINESS LTD, London, Greater London (GB)--.

Signed and Sealed this
Fourth Day of August, 2020

Andrei Iancu
*Director of the United States Patent and Trademark Office*